US012605092B2

(12) United States Patent
Stafford

(10) Patent No.: US 12,605,092 B2
(45) Date of Patent: Apr. 21, 2026

(54) INTERCONNECT FOR ON-BODY ANALYTE MONITORING DEVICE

(71) Applicant: ABBOTT DIABETES CARE INC., Alameda, CA (US)

(72) Inventor: Gary A. Stafford, Hayward, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 1013 days.

(21) Appl. No.: 17/578,952

(22) Filed: Jan. 19, 2022

(65) Prior Publication Data

US 2022/0313121 A1 Oct. 6, 2022

Related U.S. Application Data

(63) Continuation of application No. 17/137,785, filed on Dec. 30, 2020, now Pat. No. 11,259,725, which is a (Continued)

(51) Int. Cl.
*A61B 5/1477* (2006.01)
*A61B 5/00* (2006.01)

(Continued)

(52) U.S. Cl.
CPC .......... *A61B 5/1477* (2013.01); *A61B 5/0002* (2013.01); *A61B 5/14532* (2013.01); *A61B 5/14542* (2013.01); *A61B 5/14546* (2013.01); *A61B 5/14865* (2013.01); *A61B 5/742* (2013.01); *A61B 5/743* (2013.01); *C12Q 1/006* (2013.01); *H04L 67/12* (2013.01); *A61B 2560/0412* (2013.01);

(Continued)

(58) Field of Classification Search
CPC .............. A61B 5/14865; A61B 5/0002; A61B 5/14532; A61B 2562/164; A61B 2562/222; A61B 2562/22; C12Q 1/006
See application file for complete search history.

(56) References Cited

U.S. PATENT DOCUMENTS 3,211,001 A 10/1965 Petit
3,260,656 A 7/1966 Ross, Jr.
(Continued)

FOREIGN PATENT DOCUMENTS

DE 4401400 7/1995
EP 0098592 1/1984
(Continued)

OTHER PUBLICATIONS

Alcock, et al., "Continuous analyte monitoring to aid clinical practice," IEEE Engineering in Medicine & BioloXY Magazine, 13:319-25 (1994).

(Continued)

*Primary Examiner* — Christian Jang
(74) *Attorney, Agent, or Firm* — ONE LLP

(57) ABSTRACT

Disclosed herein are systems and methods for providing a compressible interconnect for allowing electrical communication between an electronics unit and an analyte sensor in an on-body analyte monitoring device. In other embodiments, systems and methods are provided for reducing the Z-height of an on-body analyte monitoring device by utilizing novel interconnects.

19 Claims, 11 Drawing Sheets

Related U.S. Application Data continuation of application No. 16/941,717, filed on Jul. 29, 2020, now abandoned, which is a continuation of application No. 15/674,439, filed on Aug. 10, 2017, now Pat. No. 10,765,351, which is a continuation of application No. 15/140,309, filed on Apr. 27, 2016, now Pat. No. 9,750,444, which is a continuation of application No. 12/895,015, filed on Sep. 30, 2010, now Pat. No. 9,351,669.

(60) Provisional application No. 61/247,516, filed on Sep. 30, 2009.

(51) Int. Cl.

| *A61B 5/145* | (2006.01) |
| *A61B 5/1486* | (2006.01) |
| *C12Q 1/00* | (2006.01) |
| *H04L 67/12* | (2022.01) |

(52) U.S. Cl.
CPC . *A61B 2560/0443* (2013.01); *A61B 2562/164* (2013.01); *A61B 2562/222* (2013.01); *A61B 2562/227* (2013.01)

(56) References Cited

U.S. PATENT DOCUMENTS

| 3,653,841 A | 4/1972 | Klein |
| 3,719,564 A | 3/1973 | Lilly et al. |
| 3,776,832 A | 12/1973 | Oswin et al. |
| 3,837,339 A | 9/1974 | Aisenberg et al. |
| 3,926,760 A | 12/1975 | Allen et al. |
| 3,949,388 A | 4/1976 | Fuller |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danninger et al. |
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,245,634 A | 1/1981 | Albisser et al. |
| 4,247,297 A | 1/1981 | Berti et al. |
| 4,294,258 A | 10/1981 | Bernard |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,450,842 A | 5/1984 | Zick et al. |
| 4,458,686 A | 7/1984 | Clark |
| 4,461,691 A | 7/1984 | Frank |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatasetty |
| 4,524,114 A | 6/1985 | Samuels et al. |
| 4,526,661 A | 7/1985 | Steckhan |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,619,754 A | 10/1986 | Niki et al. |
| 4,619,793 A | 10/1986 | Lee |
| 4,627,445 A | 12/1986 | Garcia et al. |
| 4,627,842 A | 12/1986 | Katz |
| 4,627,908 A | 12/1986 | Miller |
| 4,633,878 A | 1/1987 | Bombardieri |
| 4,637,403 A | 1/1987 | Garcia et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,671,288 A | 6/1987 | Gough |
| 4,679,562 A | 7/1987 | Luksha |
| 4,680,268 A | 7/1987 | Clark, Jr. |
| 4,682,602 A | 7/1987 | Probaska |
| 4,684,463 A | 8/1987 | Williams |
| 4,684,537 A | 8/1987 | Graetzel et al. |
| 4,685,466 A | 8/1987 | Rau |
| 4,698,057 A | 10/1987 | Joishy |
| 4,703,756 A | 11/1987 | Gough et al. |
| 4,711,245 A | 12/1987 | Higgins et al. |
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,755,173 A | 7/1988 | Konopka |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,784,736 A | 11/1988 | Lonsdale et al. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,848,351 A | 7/1989 | Finch |
| 4,854,322 A | 8/1989 | Ash et al. |
| 4,865,038 A | 9/1989 | Rich et al. |
| 4,871,351 A | 10/1989 | Feingold |

(56)        References Cited

U.S. PATENT DOCUMENTS

| | | | |
|---|---|---|---|
| 4,871,440 A | 10/1989 | Nagata et al. |
| 4,874,500 A | 10/1989 | Madou et al. |
| 4,890,620 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,921,199 A | 5/1990 | Villaveces |
| 4,923,586 A | 5/1990 | Katayama et al. |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchhouse |
| 4,935,345 A | 6/1990 | Guilbeau et al. |
| 4,938,860 A | 7/1990 | Wogoman |
| 4,944,299 A | 7/1990 | Silvian |
| 4,950,378 A | 8/1990 | Nagata |
| 4,953,552 A | 9/1990 | DeMarzo |
| 4,954,129 A | 9/1990 | Giuliano |
| 4,969,468 A | 11/1990 | Byers et al. |
| 4,970,145 A | 11/1990 | Bennetto et al. |
| 4,974,929 A | 12/1990 | Curry |
| 4,986,271 A | 1/1991 | Wilkins |
| 4,988,341 A | 1/1991 | Columbus et al. |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,013,161 A | 5/1991 | Zaragoza et al. |
| 5,019,974 A | 5/1991 | Beckers |
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,055,171 A | 10/1991 | Peck |
| 5,058,592 A | 10/1991 | Whisler |
| 5,070,535 A | 12/1991 | Hochmair et al. |
| 5,082,550 A | 1/1992 | Rishpon et al. |
| 5,082,786 A | 1/1992 | Nakamoto |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,126,034 A | 6/1992 | Carter et al. |
| 5,133,856 A | 7/1992 | Yamaguchi et al. |
| 5,135,003 A | 8/1992 | Souma |
| 5,140,985 A | 8/1992 | Schroeder et al. |
| 5,141,868 A | 8/1992 | Shanks et al. |
| 5,161,532 A | 11/1992 | Joseph |
| 5,165,407 A | 11/1992 | Wilson et al. |
| 5,174,291 A | 12/1992 | Schoonen et al. |
| 5,190,041 A | 3/1993 | Palti |
| 5,192,416 A | 3/1993 | Wang et al. |
| 5,198,367 A | 3/1993 | Aizawa et al. |
| 5,202,261 A | 4/1993 | Musho et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,229,282 A | 7/1993 | Yoshioka et al. |
| 5,234,835 A | 8/1993 | Nestor et al. |
| 5,238,729 A | 8/1993 | Debe |
| 5,246,867 A | 9/1993 | Lakowicz et al. |
| 5,250,439 A | 10/1993 | Musho et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,271,815 A | 12/1993 | Wong |
| 5,279,294 A | 1/1994 | Anderson et al. |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynch et al. |
| 5,288,636 A | 2/1994 | Pollmann et al. |
| 5,293,546 A | 3/1994 | Tadros et al. |
| 5,293,877 A | 3/1994 | O'Hara et al. |
| 5,299,571 A | 4/1994 | Mastrototaro |
| 5,320,098 A | 6/1994 | Davidson |
| 5,320,725 A | 6/1994 | Gregg et al. |
| 5,322,063 A | 6/1994 | Allen et al. |
| 5,337,747 A | 8/1994 | Neftel |
| 5,340,722 A | 8/1994 | Wolfbeis et al. |
| 5,342,789 A | 8/1994 | Chick et al. |
| 5,352,348 A | 10/1994 | Young et al. |
| 5,356,786 A | 10/1994 | Heller et al. |
| 5,360,404 A | 11/1994 | Novacek et al. |
| 5,368,028 A | 11/1994 | Palti |
| 5,372,133 A | 12/1994 | Hogen et al. |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,383,788 A * | 1/1995 | Spencer ................. H05K 1/118 |
| | | 439/493 |
| 5,387,327 A | 2/1995 | Khan |
| 5,390,670 A | 2/1995 | Centa et al. |
| 5,390,671 A | 2/1995 | Lord et al. |
| 5,391,250 A | 2/1995 | Cheney, II et al. |
| 5,395,504 A | 3/1995 | Saurer et al. |
| 5,400,782 A | 3/1995 | Beaubiah et al. |
| 5,408,999 A | 4/1995 | Singh et al. |
| 5,411,647 A | 5/1995 | Johnson et al. |
| 5,425,361 A | 6/1995 | Fenzlein et al. |
| 5,431,160 A | 7/1995 | Wilkins |
| 5,431,921 A | 7/1995 | Thombre |
| 5,437,999 A | 8/1995 | Diebold et al. |
| 5,462,645 A | 10/1995 | Albery et al. |
| 5,469,846 A | 11/1995 | Khan |
| 5,472,317 A | 12/1995 | Field et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,533,977 A | 7/1996 | Matcalf et al. |
| 5,545,191 A | 8/1996 | Mann et al. |
| 5,551,427 A | 9/1996 | Altman |
| 5,560,357 A | 10/1996 | Faupel et al. |
| 5,562,713 A | 10/1996 | Silvian |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,575,563 A | 11/1996 | Chiu et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halili et al. |
| 5,589,326 A | 12/1996 | Deng et al. |
| 5,593,852 A | 1/1997 | Heller et al. |
| 5,596,150 A | 1/1997 | Arndt et al. |
| 5,601,435 A | 2/1997 | Quy |
| 5,609,575 A | 3/1997 | Larson et al. |
| 5,617,851 A | 4/1997 | Lipkovker |
| 5,628,310 A | 5/1997 | Rao et al. |
| 5,628,890 A | 5/1997 | Carter et al. |

(56) References Cited

U.S. PATENT DOCUMENTS

| | | | |
|---|---|---|---|
| 5,632,557 A | 5/1997 | Simons |
| 5,651,869 A | 7/1997 | Yoshioka et al. |
| 5,653,239 A | 8/1997 | Pompei et al. |
| 5,660,163 A | 8/1997 | Schulman et al. |
| 5,665,222 A | 9/1997 | Heller et al. |
| 5,670,031 A | 9/1997 | Hintsche et al. |
| 5,680,858 A | 10/1997 | Hansen et al. |
| 5,682,233 A | 10/1997 | Brinda |
| 5,695,623 A | 12/1997 | Sakoda et al. |
| 5,708,247 A | 1/1998 | McAleer et al. |
| 5,711,001 A | 1/1998 | Bussan et al. |
| 5,711,861 A | 1/1998 | Ward et al. |
| 5,711,862 A | 1/1998 | Sakoda et al. |
| 5,733,044 A | 3/1998 | Rose et al. |
| D393,313 S | 4/1998 | Meisner et al. |
| 5,735,285 A | 4/1998 | Albert et al. |
| 5,741,211 A | 4/1998 | Renirie et al. |
| 5,749,656 A | 5/1998 | Boehm et al. |
| 5,766,131 A | 6/1998 | Kondo et al. |
| 5,771,001 A | 6/1998 | Cobb |
| 5,772,586 A | 6/1998 | Heinonen et al. |
| 5,779,665 A | 7/1998 | Mastrototaro et al. |
| 5,791,344 A | 8/1998 | Schulman et al. |
| 5,800,420 A | 9/1998 | Gross et al. |
| 5,807,375 A | 9/1998 | Gross et al. |
| 5,814,020 A | 9/1998 | Gross |
| 5,820,551 A | 10/1998 | Hill et al. |
| 5,820,622 A | 10/1998 | Gross et al. |
| 5,822,715 A | 10/1998 | Worthington et al. |
| 5,827,184 A | 10/1998 | Netherly et al. |
| 5,840,020 A | 11/1998 | Heinonen et al. |
| 5,842,983 A | 12/1998 | Abel et al. |
| 5,851,197 A | 12/1998 | Marano et al. |
| 5,858,001 A | 1/1999 | Tsals et al. |
| 5,865,804 A | 2/1999 | Bachynsky |
| 5,885,211 A | 3/1999 | Eppstein et al. |
| 5,899,855 A | 5/1999 | Brown |
| 5,924,979 A | 7/1999 | Sedlow et al. |
| 5,925,021 A | 7/1999 | Castellano et al. |
| 5,931,868 A | 8/1999 | Gross et al. |
| 5,938,679 A | 8/1999 | Freeman et al. |
| 5,948,006 A | 9/1999 | Mann |
| 5,951,521 A | 9/1999 | Mastrototaro et al. |
| 5,951,582 A | 9/1999 | Thorne et al. |
| 5,954,643 A | 9/1999 | Van Antwerp et al. |
| 5,954,685 A | 9/1999 | Tierney |
| 5,957,854 A | 9/1999 | Besson et al. |
| 5,961,451 A | 10/1999 | Reber et al. |
| 5,964,993 A | 10/1999 | Blubaugh et al. |
| 5,965,380 A | 10/1999 | Heller et al. |
| 5,971,922 A | 10/1999 | Arita et al. |
| 5,972,199 A | 10/1999 | Heller et al. |
| 5,987,353 A | 11/1999 | Khatchatrian et al. |
| 5,993,411 A | 11/1999 | Choi |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,022,368 A | 2/2000 | Gavronsky et al. |
| 6,024,699 A | 2/2000 | Surwit et al. |
| 6,026,321 A | 2/2000 | Miyata et al. |
| 6,027,459 A | 2/2000 | Sham et al. |
| 6,049,727 A | 4/2000 | Crothall |
| 6,056,718 A | 5/2000 | Funderburk et al. |
| 6,068,399 A | 5/2000 | Tseng |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,159,147 A | 12/2000 | Lichter et al. |
| 6,162,611 A | 12/2000 | Heller et al. |
| 6,175,752 B1 | 1/2001 | Say et al. |
| 6,186,982 B1 | 2/2001 | Gross et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,254,536 B1 | 7/2001 | DeVito |
| 6,254,586 B1 | 7/2001 | Mann et al. |
| 6,275,717 B1 | 8/2001 | Gross et al. |
| 6,283,761 B1 | 9/2001 | Joao |
| 6,283,982 B1 | 9/2001 | Levaughn et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,302,866 B1 | 10/2001 | Marggi |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,331,244 B1 | 12/2001 | Lewis et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,377,828 B1 | 4/2002 | Chaiken et al. |
| 6,379,301 B1 | 4/2002 | Worthington et al. |
| 6,409,740 B1 | 6/2002 | Kuhr et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,433,743 B1 | 8/2002 | Massy et al. |
| 6,435,017 B1 | 8/2002 | Nowicki, Jr. et al. |
| 6,437,679 B1 | 8/2002 | Rogues |
| 6,440,068 B1 | 8/2002 | Brown et al. |
| 6,445,374 B2 | 9/2002 | Albert et al. |
| 6,478,736 B1 | 11/2002 | Mault |
| 6,482,176 B1 | 11/2002 | Wich |
| 6,484,045 B1 | 11/2002 | Holker et al. |
| 6,484,046 B1 | 11/2002 | Say et al. |
| 6,514,718 B2 | 2/2003 | Heller et al. |
| 6,520,326 B2 | 2/2003 | McIvor et al. |
| 6,522,927 B1 | 2/2003 | Bishay et al. |
| 6,551,494 B1 | 4/2003 | Heller et al. |
| 6,551,496 B1 | 4/2003 | Moles et al. |
| 6,554,795 B2 | 4/2003 | Lam et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,566 B2 | 6/2003 | Effenhauser |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |

(56) References Cited

U.S. PATENT DOCUMENTS

| | | | |
|---|---|---|---|
| 6,676,290 | B1 | 1/2004 | Lu |
| 6,687,546 | B2 | 2/2004 | Lebel et al. |
| 6,689,056 | B1 | 2/2004 | Kilcoyne et al. |
| 6,694,191 | B2 | 2/2004 | Starkweather et al. |
| 6,695,860 | B1 | 2/2004 | Ward et al. |
| 6,702,857 | B2 | 3/2004 | Brauker et al. |
| 6,733,446 | B2 | 5/2004 | Lebel et al. |
| 6,740,075 | B2 | 5/2004 | Lebel et al. |
| 6,741,877 | B1 | 5/2004 | Shults et al. |
| 6,746,582 | B2 | 6/2004 | Heller et al. |
| 6,758,810 | B2 | 7/2004 | Lebel et al. |
| 6,770,030 | B1 | 8/2004 | Schaupp et al. |
| 6,790,178 | B1 | 9/2004 | Mault et al. |
| 6,809,653 | B1 | 10/2004 | Mann et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,813,519 | B2 | 11/2004 | Lebel et al. |
| 6,830,551 | B1 | 12/2004 | Uchigaki et al. |
| 6,837,858 | B2 | 1/2005 | Cunningham et al. |
| 6,837,988 | B2 | 1/2005 | Leong et al. |
| 6,849,052 | B2 | 2/2005 | Ughigaki et al. |
| 6,854,882 | B2 | 2/2005 | Chen |
| 6,862,465 | B2 | 3/2005 | Shults et al. |
| 6,873,268 | B2 | 3/2005 | Lebel et al. |
| 6,881,551 | B2 | 4/2005 | Heller et al. |
| 6,892,085 | B2 | 5/2005 | McIvor et al. |
| 6,895,265 | B2 | 5/2005 | Silver |
| 6,931,327 | B2 | 8/2005 | Goode, Jr. et al. |
| 6,932,894 | B2 | 8/2005 | Mao et al. |
| 6,936,006 | B2 | 8/2005 | Sabra |
| 6,942,518 | B2 | 9/2005 | Liamos et al. |
| 6,950,708 | B2 | 9/2005 | Bowman IV et al. |
| 6,958,705 | B2 | 10/2005 | Lebel et al. |
| 6,959,211 | B2 | 10/2005 | Rule et al. |
| 6,968,294 | B2 | 11/2005 | Gutta et al. |
| 6,971,274 | B2 | 12/2005 | Olin |
| 6,971,999 | B2 | 12/2005 | Py et al. |
| 6,974,437 | B2 | 12/2005 | Lebel et al. |
| 6,990,366 | B2 | 1/2006 | Say et al. |
| 6,997,907 | B2 | 2/2006 | Safabash et al. |
| 6,998,247 | B2 | 2/2006 | Monfre et al. |
| 7,003,336 | B2 | 2/2006 | Holker et al. |
| 7,003,340 | B2 | 2/2006 | Say et al. |
| 7,003,341 | B2 | 2/2006 | Say et al. |
| 7,024,245 | B2 | 4/2006 | Lebel et al. |
| 7,025,743 | B2 | 4/2006 | Mann et al. |
| 7,041,068 | B2 | 5/2006 | Freeman et al. |
| 7,041,468 | B2 | 5/2006 | Drucker et al. |
| 7,052,483 | B2 | 5/2006 | Wojcik |
| 7,056,302 | B2 | 6/2006 | Douglas |
| 7,074,307 | B2 | 7/2006 | Simpson et al. |
| 7,081,195 | B2 | 7/2006 | Simpson et al. |
| 7,097,637 | B2 | 8/2006 | Triplett et al. |
| 7,098,803 | B2 | 8/2006 | Mann et al. |
| 7,108,778 | B2 | 9/2006 | Simpson et al. |
| 7,110,803 | B2 | 9/2006 | Shults et al. |
| 7,113,821 | B1 | 9/2006 | Sun et al. |
| 7,134,999 | B2 | 11/2006 | Brauker et al. |
| 7,136,689 | B2 | 11/2006 | Shults et al. |
| 7,171,274 | B2 | 1/2007 | Starkweather et al. |
| 7,190,988 | B2 | 3/2007 | Say et al. |
| 7,192,450 | B2 | 3/2007 | Brauker et al. |
| 7,198,606 | B2 | 4/2007 | Boecker et al. |
| 7,207,974 | B2 | 4/2007 | Safabash et al. |
| 7,226,978 | B2 | 6/2007 | Tapsak et al. |
| 7,276,029 | B2 | 10/2007 | Goode, Jr. et al. |
| 7,278,983 | B2 | 10/2007 | Ireland et al. |
| 7,297,151 | B2 | 11/2007 | Boecker et al. |
| 7,299,082 | B2 | 11/2007 | Feldman et al. |
| 7,310,544 | B2 | 12/2007 | Brister et al. |
| 7,318,816 | B2 | 1/2008 | Bobroff et al. |
| 7,324,012 | B2 | 1/2008 | Mann et al. |
| 7,329,239 | B2 | 2/2008 | Safabash et al. |
| 7,335,294 | B2 | 2/2008 | Heller et al. |
| 7,340,309 | B2 | 3/2008 | Miazga et al. |
| 7,354,420 | B2 | 4/2008 | Steil et al. |
| 7,364,592 | B2 | 4/2008 | Carr-Brendel et al. |
| 7,366,556 | B2 | 4/2008 | Brister et al. |
| 7,379,765 | B2 | 5/2008 | Petisce et al. |
| 7,381,184 | B2 | 6/2008 | Funderburk et al. |
| 7,402,153 | B2 | 7/2008 | Steil et al. |
| 7,416,541 | B2 | 8/2008 | Yuzhakov et al. |
| 7,424,318 | B2 | 9/2008 | Brister et al. |
| 7,455,663 | B2 | 11/2008 | Bikovsky |
| 7,460,898 | B2 | 12/2008 | Brister et al. |
| 7,462,264 | B2 | 12/2008 | Heller et al. |
| 7,467,003 | B2 | 12/2008 | Brister et al. |
| 7,471,972 | B2 | 12/2008 | Rhodes et al. |
| 7,494,465 | B2 | 2/2009 | Brister et al. |
| 7,497,827 | B2 | 3/2009 | Brister et al. |
| 7,499,002 | B2 | 3/2009 | Blasko et al. |
| 7,519,408 | B2 | 4/2009 | Rasdal et al. |
| 7,583,990 | B2 | 9/2009 | Goode, Jr. et al. |
| 7,591,801 | B2 | 9/2009 | Brauker et al. |
| 7,599,726 | B2 | 10/2009 | Goode, Jr. et al. |
| 7,604,592 | B2 | 10/2009 | Freeman et al. |
| 7,613,491 | B2 | 11/2009 | Boock et al. |
| 7,615,007 | B2 | 11/2009 | Shults et al. |
| 7,632,228 | B2 | 12/2009 | Brauker et al. |
| 7,637,868 | B2 | 12/2009 | Saint et al. |
| 7,640,048 | B2 | 12/2009 | Dobbles et al. |
| 7,651,596 | B2 | 1/2010 | Petisce et al. |
| 7,654,956 | B2 | 2/2010 | Brister et al. |
| 7,657,297 | B2 | 2/2010 | Simpson et al. |
| 7,666,149 | B2 | 2/2010 | Simons et al. |
| 7,697,967 | B2 | 4/2010 | Stafford |
| 7,705,653 | B2 | 4/2010 | Schell |
| 7,705,980 | B2 | 4/2010 | Smous et al. |
| 7,711,402 | B2 | 5/2010 | Shults et al. |
| 7,713,574 | B2 | 5/2010 | Brister et al. |
| 7,715,893 | B2 | 5/2010 | Kamath et al. |
| 7,722,536 | B2 | 5/2010 | Godnow et al. |
| 7,727,147 | B1 | 6/2010 | Osorio et al. |
| 7,731,657 | B2 | 6/2010 | Stafford |
| 7,736,344 | B2 | 6/2010 | Moberg et al. |
| 7,741,734 | B2 | 6/2010 | Joannopoulos et al. |
| 7,763,042 | B2 | 7/2010 | Iio et al. |
| 7,766,829 | B2 | 8/2010 | Sloan et al. |
| 7,771,352 | B2 | 8/2010 | Shults et al. |
| 7,774,145 | B2 | 8/2010 | Brauker et al. |
| 7,775,444 | B2 | 8/2010 | DeRocco et al. |
| 7,779,332 | B2 | 8/2010 | Karr et al. |
| 7,780,827 | B1 | 8/2010 | Bhullar et al. |
| 7,782,192 | B2 | 8/2010 | Jeckelmann et al. |
| 7,783,333 | B2 | 8/2010 | Brister et al. |
| 7,791,467 | B2 | 9/2010 | Mazar et al. |
| 7,792,562 | B2 | 9/2010 | Shults et al. |
| 7,822,454 | B1 | 10/2010 | Alden et al. |
| 7,826,981 | B2 | 11/2010 | Goode et al. |
| 7,831,310 | B2 | 11/2010 | Lebel et al. |
| 7,860,574 | B2 | 12/2010 | Von Arx et al. |
| 7,873,299 | B2 | 1/2011 | Berner et al. |
| 7,882,611 | B2 | 2/2011 | Shah et al. |
| 7,883,464 | B2 | 2/2011 | Stafford |
| 7,899,511 | B2 | 3/2011 | Shults et al. |
| 7,905,833 | B2 | 3/2011 | Brister et al. |
| 7,912,674 | B2 | 3/2011 | Killoren Clark et al. |
| 7,914,460 | B2 | 3/2011 | Melker et al. |
| 7,920,907 | B2 | 4/2011 | McGarraugh et al. |
| 7,946,985 | B2 | 5/2011 | Mastrototaro et al. |
| 7,955,258 | B2 | 6/2011 | Goscha et al. |
| 7,970,448 | B2 | 6/2011 | Shults et al. |
| 7,974,672 | B2 | 7/2011 | Shults et al. |
| 7,976,466 | B2 | 7/2011 | Ward et al. |
| 7,999,674 | B2 | 8/2011 | Kamen |
| 8,010,174 | B2 | 8/2011 | Goode et al. |
| 8,072,310 | B1 | 12/2011 | Everhart |
| 8,090,445 | B2 | 1/2012 | Ginggen |
| 8,093,991 | B2 | 1/2012 | Stevenson et al. |
| 8,094,009 | B2 | 1/2012 | Allen et al. |
| 8,098,159 | B2 | 1/2012 | Batra et al. |
| 8,098,160 | B2 | 1/2012 | Howarth et al. |
| 8,098,161 | B2 | 1/2012 | Lavedas |

(56) References Cited

U.S. PATENT DOCUMENTS

| | | | |
|---|---|---|---|
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,112,240 B2 | 2/2012 | Fennell |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,150,321 B2 | 4/2012 | Winter et al. |
| 8,150,516 B2 | 4/2012 | Levine et al. |
| 8,179,266 B2 | 5/2012 | Hermle |
| 8,180,423 B2 | 5/2012 | Mang et al. |
| 8,373,544 B2 | 2/2013 | Pitt-Pladdy |
| 8,512,243 B2 | 8/2013 | Stafford |
| 8,515,518 B2 | 8/2013 | Ouyang et al. |
| 8,545,403 B2 | 10/2013 | Peyser et al. |
| 8,585,591 B2 | 11/2013 | Sloan et al. |
| 8,602,991 B2 | 12/2013 | Stafford |
| 8,617,071 B2 | 12/2013 | Say et al. |
| 8,622,903 B2 | 1/2014 | Jin et al. |
| 8,628,498 B2 | 1/2014 | Safabash et al. |
| 8,652,043 B2 | 2/2014 | Drucker et al. |
| 8,684,930 B2 | 4/2014 | Feldman et al. |
| 8,692,655 B2 | 4/2014 | Zimman et al. |
| 8,771,183 B2 | 7/2014 | Sloan |
| 8,797,163 B2 | 8/2014 | Finkenzeller |
| 8,961,413 B2 | 2/2015 | Teller et al. |
| 9,014,774 B2 | 4/2015 | Mao et al. |
| 9,031,630 B2 | 5/2015 | Hoss et al. |
| 9,060,805 B2 | 6/2015 | Goodnow et al. |
| 9,066,697 B2 | 6/2015 | Peyser et al. |
| 9,402,544 B2 | 8/2016 | Yee et al. |
| 2001/0011224 A1 | 8/2001 | Brown |
| 2001/0037060 A1 | 11/2001 | Thompson et al. |
| 2001/0039504 A1 | 11/2001 | Linberg et al. |
| 2001/0049231 A1* | 12/2001 | Bricaud ............ H01R 13/2442 |
| | | 439/630 |
| 2001/0054217 A1 | 12/2001 | Wang |
| 2002/0013538 A1 | 1/2002 | Teller |
| 2002/0019022 A1 | 2/2002 | Dunn et al. |
| 2002/0022855 A1 | 2/2002 | Bobroff et al. |
| 2002/0023852 A1 | 2/2002 | McIvor et al. |
| 2002/0026111 A1 | 2/2002 | Ackerman |
| 2002/0029157 A1 | 3/2002 | Marchosky |
| 2002/0042090 A1 | 4/2002 | Heller et al. |
| 2002/0049617 A1 | 4/2002 | Lencki et al. |
| 2002/0054320 A1 | 5/2002 | Ogino |
| 2002/0055711 A1 | 5/2002 | Lavi et al. |
| 2002/0055855 A1 | 5/2002 | Cule et al. |
| 2002/0072784 A1 | 6/2002 | Sheppard et al. |
| 2002/0072858 A1 | 6/2002 | Cheng |
| 2002/0076966 A1 | 6/2002 | Carron et al. |
| 2002/0082487 A1 | 6/2002 | Kollias et al. |
| 2002/0082850 A1 | 6/2002 | Panelli |
| 2002/0103499 A1 | 8/2002 | Perez et al. |
| 2002/0106709 A1 | 8/2002 | Potts et al. |
| 2002/0107476 A1 | 8/2002 | Mann et al. |
| 2002/0111832 A1 | 8/2002 | Judge |
| 2002/0119711 A1 | 8/2002 | VanAntwerp et al. |
| 2002/0128594 A1 | 9/2002 | Das et al. |
| 2002/0130042 A1 | 9/2002 | Kuhr et al. |
| 2002/0133066 A1 | 9/2002 | Miller et al. |
| 2002/0154050 A1 | 10/2002 | Krupp et al. |
| 2002/0161288 A1 | 10/2002 | Shin et al. |
| 2002/0161290 A1 | 10/2002 | Chance |
| 2002/0165462 A1 | 11/2002 | Westbrook et al. |
| 2002/0169369 A1 | 11/2002 | Ward et al. |
| 2002/0169635 A1 | 11/2002 | Shillingburg |
| 2002/0170148 A1 | 11/2002 | Mayne et al. |
| 2002/0188424 A1 | 12/2002 | Grinstein et al. |
| 2002/0188748 A1 | 12/2002 | Blackwell et al. |
| 2002/0198444 A1 | 12/2002 | Ughigaki et al. |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0038047 A1 | 2/2003 | Sleva et al. |
| 2003/0040661 A1 | 2/2003 | Abraham et al. |
| 2003/0040821 A1 | 2/2003 | Case |
| 2003/0042137 A1 | 3/2003 | Mao et al. |
| 2003/0047575 A1 | 3/2003 | Enkerlin et al. |
| 2003/0053665 A1 | 3/2003 | Hamid |
| 2003/0055679 A1 | 3/2003 | Soll et al. |
| 2003/0058245 A1 | 3/2003 | Brazhnik et al. |
| 2003/0060692 A1 | 3/2003 | Ruchti et al. |
| 2003/0060753 A1 | 3/2003 | Starkweather et al. |
| 2003/0063524 A1 | 4/2003 | Niemiec et al. |
| 2003/0064751 A1 | 4/2003 | Charlier et al. |
| 2003/0065308 A1 | 4/2003 | Lebel et al. |
| 2003/0065534 A1 | 4/2003 | McCartney |
| 2003/0069510 A1 | 4/2003 | Semler |
| 2003/0069753 A1 | 4/2003 | Brown |
| 2003/0078481 A1 | 4/2003 | McIvor et al. |
| 2003/0078560 A1 | 4/2003 | Miller et al. |
| 2003/0088238 A1 | 5/2003 | Poulsen et al. |
| 2003/0097092 A1 | 5/2003 | Flaherty |
| 2003/0097279 A1 | 5/2003 | deLusignan et al. |
| 2003/0100040 A1 | 5/2003 | Bonnecaze et al. |
| 2003/0100821 A1 | 5/2003 | Heller et al. |
| 2003/0106917 A1 | 6/2003 | Shetler et al. |
| 2003/0109775 A1 | 6/2003 | O'Neil et al. |
| 2003/0110059 A1 | 6/2003 | Janas et al. |
| 2003/0120516 A1 | 6/2003 | Perednia |
| 2003/0134347 A1 | 7/2003 | Heller et al. |
| 2003/0135333 A1 | 7/2003 | Aceti et al. |
| 2003/0144581 A1 | 7/2003 | Conn et al. |
| 2003/0144608 A1 | 7/2003 | Kojima et al. |
| 2003/0155656 A1 | 8/2003 | Chiu |
| 2003/0158707 A1 | 8/2003 | Doi |
| 2003/0158754 A1 | 8/2003 | Elkind |
| 2003/0163351 A1 | 8/2003 | Brown et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199739 A1 | 10/2003 | Gordon et al. |
| 2003/0199790 A1 | 10/2003 | Boecker et al. |
| 2003/0199910 A1 | 10/2003 | Boecker et al. |
| 2003/0208110 A1 | 11/2003 | Mault et al. |
| 2003/0208113 A1 | 11/2003 | Mault et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0225324 A1 | 12/2003 | Anderson et al. |
| 2003/0225361 A1 | 12/2003 | Sabra |
| 2003/0229514 A2 | 12/2003 | Brown |
| 2003/0231552 A1 | 12/2003 | Markart |
| 2003/0233257 A1 | 12/2003 | Matian et al. |
| 2003/0236738 A1 | 12/2003 | Lange et al. |
| 2004/0002682 A1 | 1/2004 | Kovelman et al. |
| 2004/0010207 A1 | 1/2004 | Flaherty et al. |
| 2004/0011671 A1 | 1/2004 | Shults et al. |
| 2004/0014069 A1 | 1/2004 | Cohen et al. |
| 2004/0035897 A1 | 2/2004 | Salentine et al. |

(56)                  References Cited

U.S. PATENT DOCUMENTS

2004/0039298 A1    2/2004   Abreu
2004/0040840 A1    3/2004   Mao et al.
2004/0041749 A1    3/2004   Dixon
2004/0044548 A1    3/2004   Marshall et al.
2004/0045879 A1    3/2004   Shults et al.
2004/0054263 A1    3/2004   Moerman et al.
2004/0056055 A1    3/2004   Folmer
2004/0059201 A1    3/2004   Ginsberg
2004/0063435 A1    4/2004   Sakamoto et al.
2004/0064068 A1    4/2004   DeNuzzio et al.
2004/0072357 A1    4/2004   Steine et al.
2004/0073266 A1    4/2004   Haefner et al.
2004/0078215 A1    4/2004   Dahlin et al.
2004/0096959 A1    5/2004   Steine et al.
2004/0106858 A1    6/2004   Say et al.
2004/0106859 A1    6/2004   Say et al.
2004/0116847 A1    6/2004   Wall
2004/0116866 A1    6/2004   Gorman et al.
2004/0122353 A1    6/2004   Shahmirian et al.
2004/0122489 A1    6/2004   Mazar et al.
2004/0133164 A1    7/2004   Funderburk et al.
2004/0133462 A1    7/2004   Smith et al.
2004/0135684 A1    7/2004   Steinthal et al.
2004/0138544 A1    7/2004   Ward et al.
2004/0138588 A1    7/2004   Saikley et al.
2004/0138688 A1    7/2004   Giraud
2004/0140211 A1    7/2004   Broy et al.
2004/0146909 A1    7/2004   Duong et al.
2004/0147996 A1    7/2004   Miazga et al.
2004/0152622 A1    8/2004   Keith et al.
2004/0152961 A1    8/2004   Carlson et al.
2004/0155079 A1    8/2004   Shetler et al.
2004/0158207 A1    8/2004   Hunn et al.
2004/0165211 A1    8/2004   Herrmann et al.
2004/0167801 A1    8/2004   Say et al.
2004/0171910 A1    9/2004   Moore-Steele
2004/0171921 A1    9/2004   Say et al.
2004/0172284 A1    9/2004   Sullivan et al.
2004/0172307 A1    9/2004   Gruber
2004/0176672 A1    9/2004   Silver et al.
2004/0176913 A1    9/2004   Kawatahara et al.
2004/0186362 A1    9/2004   Brauker et al.
2004/0186365 A1    9/2004   Jin et al.
2004/0193090 A1    9/2004   Lebel et al.
2004/0195284 A1    10/2004  Iitsuka
2004/0197846 A1    10/2004  Hockersmith et al.
2004/0199059 A1    10/2004  Brauker et al.
2004/0199409 A1    10/2004  Brown
2004/0200867 A1    10/2004  Chee
2004/0204687 A1    10/2004  Mogensen et al.
2004/0204863 A1    10/2004  Kim et al.
2004/0204868 A1    10/2004  Maynard et al.
2004/0210458 A1    10/2004  Evans et al.
2004/0223985 A1    11/2004  Dunfiled et al.
2004/0225338 A1    11/2004  Lebel et al.
2004/0232180 A1    11/2004  Badillo
2004/0236200 A1    11/2004  Say et al.
2004/0236251 A1    11/2004  Roe et al.
2004/0254433 A1    12/2004  Bandis et al.
2004/0254434 A1    12/2004  Goodnow et al.
2004/0260155 A1    12/2004  Ciarniello et al.
2004/0260478 A1    12/2004  Schwamm
2004/0267300 A1    12/2004  Mace
2005/0003470 A1    1/2005   Nelson et al.
2005/0004439 A1    1/2005   Shin et al.
2005/0004494 A1    1/2005   Perez et al.
2005/0006122 A1    1/2005   Burnette
2005/0010269 A1    1/2005   Lebel et al.
2005/0022274 A1    1/2005   Campbell et al.
2005/0023137 A1    2/2005   Bhullar et al.
2005/0027177 A1    2/2005   Shin et al.
2005/0027180 A1    2/2005   Goode, Jr. et al.
2005/0031689 A1    2/2005   Shults et al.
2005/0038680 A1    2/2005   McMahon
2005/0043598 A1    2/2005   Goode, Jr. et al.

2005/0045685 A1    3/2005   Goode, Jr. et al.
2005/0048194 A1    3/2005   Sesto
2005/0049179 A1    3/2005   Davidson et al.
2005/0055243 A1    3/2005   Shmulewitz
2005/0059873 A1    3/2005   Arndt et al.
2005/0065555 A1    3/2005   Er
2005/0070819 A1    3/2005   Poux et al.
2005/0071752 A1    3/2005   Marlatt
2005/0085872 A1    4/2005   Yanagihara et al.
2005/0090607 A1    4/2005   Tapsak et al.
2005/0090850 A1    4/2005   Thoes et al.
2005/0092791 A1    5/2005   Labarca et al.
2005/0096511 A1    5/2005   Fox et al.
2005/0096512 A1    5/2005   Fox et al.
2005/0096520 A1    5/2005   Maekawa et al.
2005/0106713 A1    5/2005   Phan et al.
2005/0112169 A1    5/2005   Brauker et al.
2005/0113653 A1    5/2005   Fox et al.
2005/0114068 A1    5/2005   Chey et al.
2005/0116683 A1    6/2005   Cheng et al.
2005/0121322 A1    6/2005   Say et al.
2005/0131311 A1    6/2005   Leuthardt et al.
2005/0131346 A1    6/2005   Douglas
2005/0137530 A1    6/2005   Campbell et al.
2005/0143635 A1    6/2005   Kamath et al.
2005/0154271 A1    7/2005   Rasdal et al.
2005/0154410 A1    7/2005   Conway et al.
2005/0165404 A1    7/2005   Miller
2005/0171512 A1    8/2005   Flaherty
2005/0173245 A1    8/2005   Feldman et al.
2005/0176136 A1    8/2005   Burd et al.
2005/0177398 A1    8/2005   Watanabe et al.
2005/0182306 A1    8/2005   Sloan
2005/0182366 A1    8/2005   Vogt et al.
2005/0187720 A1    8/2005   Goode, Jr. et al.
2005/0192557 A1    9/2005   Brauker et al.
2005/0195930 A1    9/2005   Spital et al.
2005/0197554 A1    9/2005   Polcha
2005/0199494 A1    9/2005   Say et al.
2005/0203360 A1    9/2005   Brauker et al.
2005/0203461 A1    9/2005   Flaherty et al.
2005/0203707 A1    9/2005   Tsutsui et al.
2005/0222518 A1    10/2005  Dib
2005/0222599 A1    10/2005  Czernecki et al.
2005/0236277 A9    10/2005  Imran et al.
2005/0238507 A1    10/2005  Dilanni et al.
2005/0239154 A1    10/2005  Feldman et al.
2005/0239156 A1    10/2005  Drucker et al.
2005/0241957 A1    11/2005  Mao et al.
2005/0245795 A1    11/2005  Goode, Jr. et al.
2005/0245799 A1    11/2005  Brauker et al.
2005/0245839 A1    11/2005  Stivoric et al.
2005/0245844 A1    11/2005  Mace et al.
2005/0256417 A1    11/2005  Rischell et al.
2005/0260174 A1    11/2005  Fraser et al.
2005/0261558 A1    11/2005  Eaton et al.
2005/0267327 A1    12/2005  Iizuka et al.
2005/0267780 A1    12/2005  Ray et al.
2005/0271996 A1    12/2005  Sporbert et al.
2005/0277164 A1    12/2005  Drucker et al.
2005/0281234 A1    12/2005  Kawamura et al.
2005/0281706 A1    12/2005  Funke et al.
2005/0283114 A1    12/2005  Bresina et al.
2005/0283386 A1    12/2005  Powers et al.
2005/0287620 A1    12/2005  Heller et al.
2005/0288571 A1    12/2005  Perkins et al.
2006/0001538 A1    1/2006   Kraft et al.
2006/0001551 A1    1/2006   Kraft et al.
2006/0004270 A1    1/2006   Bedard et al.
2006/0004303 A1    1/2006   Weidenhaupt et al.
2006/0004603 A1    1/2006   Peterka et al.
2006/0004607 A1    1/2006   Marshall et al.
2006/0006141 A1    1/2006   Ufer et al.
2006/0010098 A1    1/2006   Goodnow et al.
2006/0015020 A1    1/2006   Neale et al.
2006/0015024 A1    1/2006   Brister et al.
2006/0016700 A1    1/2006   Brister et al.
2006/0019327 A1    1/2006   Brister et al.
2006/0020186 A1    1/2006   Brister et al.

(56)          References Cited

U.S. PATENT DOCUMENTS

| | | |
|---|---|---|
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0029177 A1 | 2/2006 | Cranford, Jr. et al. |
| 2006/0031094 A1 | 2/2006 | Cohen et al. |
| 2006/0036134 A1 | 2/2006 | Tarassenko et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0041229 A1 | 2/2006 | Garibotto et al. |
| 2006/0047220 A1 | 3/2006 | Sokoto et al. |
| 2006/0051738 A1 | 3/2006 | Zweig |
| 2006/0058612 A1 | 3/2006 | Dave et al. |
| 2006/0058626 A1 | 3/2006 | Weiss et al. |
| 2006/0063135 A1 | 3/2006 | Mehl |
| 2006/0079740 A1 | 4/2006 | Silver et al. |
| 2006/0094952 A1 | 5/2006 | Ma et al. |
| 2006/0095225 A1 | 5/2006 | Harmon et al. |
| 2006/0115790 A1 | 6/2006 | Alon et al. |
| 2006/0129173 A1 | 6/2006 | Wilkinson |
| 2006/0129328 A1 | 6/2006 | Leo et al. |
| 2006/0143041 A1 | 6/2006 | Tipirneni |
| 2006/0154642 A1 | 7/2006 | Scannell |
| 2006/0155180 A1 | 7/2006 | Brister et al. |
| 2006/0155210 A1 | 7/2006 | Beckman et al. |
| 2006/0155317 A1 | 7/2006 | List |
| 2006/0166629 A1 | 7/2006 | Reggiardo |
| 2006/0167718 A1 | 7/2006 | Tischer |
| 2006/0173260 A1 | 8/2006 | Gaoni et al. |
| 2006/0173444 A1 | 8/2006 | Choy et al. |
| 2006/0178633 A1 | 8/2006 | Garibotto et al. |
| 2006/0183985 A1 | 8/2006 | Brister et al. |
| 2006/0189863 A1 | 8/2006 | Peyser et al. |
| 2006/0189939 A1 | 8/2006 | Gononelli et al. |
| 2006/0195029 A1 | 8/2006 | Shults et al. |
| 2006/0200970 A1 | 9/2006 | Brister et al. |
| 2006/0202805 A1 | 9/2006 | Schulman et al. |
| 2006/0222566 A1 | 10/2006 | Brauker et al. |
| 2006/0224141 A1 | 10/2006 | Rush et al. |
| 2006/0226985 A1 | 10/2006 | Goodnow et al. |
| 2006/0235009 A1 | 10/2006 | Glickman et al. |
| 2006/0240549 A1 | 10/2006 | Minton |
| 2006/0241969 A1 | 10/2006 | Wilhide et al. |
| 2006/0244465 A1 | 11/2006 | Kroh et al. |
| 2006/0247508 A1 | 11/2006 | Fennell |
| 2006/0247710 A1 | 11/2006 | Goetz et al. |
| 2006/0258929 A1 | 11/2006 | Goode, Jr. et al. |
| 2006/0264888 A1 | 11/2006 | Moberg et al. |
| 2006/0272652 A1 | 12/2006 | Stocker et al. |
| 2006/0276724 A1 | 12/2006 | Freeman et al. |
| 2006/0282042 A1 | 12/2006 | Walters et al. |
| 2006/0282290 A1 | 12/2006 | Flaherty et al. |
| 2006/0287691 A1 | 12/2006 | Drew |
| 2007/0010950 A1 | 1/2007 | Abensour et al. |
| 2007/0012324 A1 | 1/2007 | Nirkondar et al. |
| 2007/0016381 A1 | 1/2007 | Kamath et al. |
| 2007/0016449 A1 | 1/2007 | Cohen et al. |
| 2007/0027381 A1 | 2/2007 | Stafford |
| 2007/0033074 A1 | 2/2007 | Nitzan et al. |
| 2007/0033114 A1 | 2/2007 | Minor |
| 2007/0038044 A1 | 2/2007 | Dobbles et al. |
| 2007/0041626 A1 | 2/2007 | Weiss et al. |
| 2007/0055799 A1 | 3/2007 | Koehler et al. |
| 2007/0060814 A1 | 3/2007 | Stafford |
| 2007/0060979 A1 | 3/2007 | Strother et al. |
| 2007/0061170 A1 | 3/2007 | Lorsch et al. |
| 2007/0066873 A1 | 3/2007 | Kamath et al. |
| 2007/0066956 A1 | 3/2007 | Finkel |
| 2007/0067000 A1 | 3/2007 | Strother et al. |
| 2007/0071681 A1 | 3/2007 | Gadkar et al. |
| 2007/0073129 A1* | 3/2007 | Shah .................... A61B 5/6849 |
| | | 600/347 |
| 2007/0074043 A1 | 3/2007 | Lacey |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0078818 A1 | 4/2007 | Zvitz et al. |
| 2007/0093786 A1 | 4/2007 | Goldsmith et al. |
| 2007/0095661 A1 | 5/2007 | Wang et al. |
| 2007/0096715 A1 | 5/2007 | Joy et al. |
| 2007/0100215 A1 | 5/2007 | Powers et al. |
| 2007/0106135 A1 | 5/2007 | Sloan et al. |
| 2007/0110124 A1 | 5/2007 | Shiraki et al. |
| 2007/0118405 A1 | 5/2007 | Campbell et al. |
| 2007/0123819 A1 | 5/2007 | Mernoe et al. |
| 2007/0124002 A1 | 5/2007 | Estes et al. |
| 2007/0149861 A1 | 6/2007 | Crothall et al. |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173698 A1 | 7/2007 | Kivela et al. |
| 2007/0173706 A1 | 7/2007 | Neinast et al. |
| 2007/0173741 A1 | 7/2007 | Deshmukh et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0185390 A1 | 8/2007 | Perkins et al. |
| 2007/0191701 A1 | 8/2007 | Feldman et al. |
| 2007/0203407 A1 | 8/2007 | Hoss et al. |
| 2007/0203539 A1 | 8/2007 | Stone et al. |
| 2007/0203966 A1 | 8/2007 | Brauker et al. |
| 2007/0213611 A1 | 9/2007 | Simpson et al. |
| 2007/0219432 A1 | 9/2007 | Thompson |
| 2007/0219480 A1 | 9/2007 | Kamen et al. |
| 2007/0219597 A1 | 9/2007 | Kamen et al. |
| 2007/0228071 A1 | 10/2007 | Kamen et al. |
| 2007/0231846 A1 | 10/2007 | Cosentino et al. |
| 2007/0232880 A1 | 10/2007 | Siddiqui et al. |
| 2007/0235331 A1 | 10/2007 | Simpson et al. |
| 2007/0244368 A1 | 10/2007 | Bayloff et al. |
| 2007/0244379 A1 | 10/2007 | Boock et al. |
| 2007/0244383 A1 | 10/2007 | Talbot et al. |
| 2007/0244398 A1 | 10/2007 | Lo et al. |
| 2007/0249921 A1* | 10/2007 | Groll .................. G01N 27/3273 |
| | | 600/347 |
| 2007/0249922 A1 | 10/2007 | Peyser et al. |
| 2007/0253021 A1 | 11/2007 | Mehta et al. |
| 2007/0255302 A1 | 11/2007 | Koeppel et al. |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |
| 2007/0293932 A1 | 12/2007 | Zilla et al. |
| 2008/0004512 A1 | 1/2008 | Funderburk et al. |
| 2008/0004573 A1 | 1/2008 | Kaufmann et al. |
| 2008/0004904 A1 | 1/2008 | Tran |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0021666 A1 | 1/2008 | Goode, Jr. et al. |
| 2008/0026338 A1 | 1/2008 | Cinader |
| 2008/0027474 A1 | 1/2008 | Curry et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0033268 A1 | 2/2008 | Stafford |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0057484 A1 | 3/2008 | Miyata et al. |
| 2008/0058626 A1 | 3/2008 | Miyata et al. |
| 2008/0058678 A1 | 3/2008 | Miyata et al. |
| 2008/0062891 A1 | 3/2008 | Van der Merwe et al. |
| 2008/0063948 A1 | 3/2008 | O'Brien |

(56)        References Cited

U.S. PATENT DOCUMENTS

| 2008/0064937 A1 | 3/2008 | McGarraugh et al. |
| 2008/0064941 A1 | 3/2008 | Funderburk et al. |
| 2008/0064943 A1 | 3/2008 | Talbot et al. |
| 2008/0065236 A1 | 3/2008 | Bristol |
| 2008/0065646 A1 | 3/2008 | Zhang et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0071580 A1 | 3/2008 | Marcus et al. |
| 2008/0073993 A1 | 3/2008 | Sortore et al. |
| 2008/0077433 A1 | 3/2008 | Kasprisin et al. |
| 2008/0078567 A1 | 4/2008 | Miller et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097246 A1 | 4/2008 | Stafford |
| 2008/0097289 A1 | 4/2008 | Steil et al. |
| 2008/0099332 A1 | 5/2008 | Scott et al. |
| 2008/0105479 A1 | 5/2008 | Lei |
| 2008/0105748 A1 | 5/2008 | Lei |
| 2008/0108942 A1 | 5/2008 | Brister et al. |
| 2008/0112848 A1 | 5/2008 | Huffstodt et al. |
| 2008/0114228 A1 | 5/2008 | McCluskey et al. |
| 2008/0114280 A1 | 5/2008 | Stafford |
| 2008/0119705 A1 | 5/2008 | Patel et al. |
| 2008/0119707 A1 | 5/2008 | Stafford |
| 2008/0125636 A1 | 5/2008 | Ward et al. |
| 2008/0126882 A1 | 5/2008 | Fulton et al. |
| 2008/0127052 A1 | 5/2008 | Rostoker |
| 2008/0129465 A1 | 6/2008 | Rao |
| 2008/0133702 A1 | 6/2008 | Sharma et al. |
| 2008/0139910 A1 | 6/2008 | Mastrototaro et al. |
| 2008/0145277 A1 | 6/2008 | Wohland |
| 2008/0154513 A1 | 6/2008 | Kovatchev et al. |
| 2008/0167543 A1 | 7/2008 | Say et al. |
| 2008/0167572 A1 | 7/2008 | Stivoric et al. |
| 2008/0167578 A1 | 7/2008 | Bryer et al. |
| 2008/0172205 A1 | 7/2008 | Breton et al. |
| 2008/0183060 A1 | 7/2008 | Steil et al. |
| 2008/0183061 A1 | 7/2008 | Goode, Jr. et al. |
| 2008/0183399 A1 | 7/2008 | Goode, Jr. et al. |
| 2008/0183500 A1 | 7/2008 | Banigan |
| 2008/0188731 A1 | 8/2008 | Brister et al. |
| 2008/0188796 A1 | 8/2008 | Steil et al. |
| 2008/0189051 A1 | 8/2008 | Goode, Jr. et al. |
| 2008/0194934 A1 | 8/2008 | Ray et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0208025 A1 | 8/2008 | Shults et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0235469 A1 | 9/2008 | Drew |
| 2008/0242961 A1 | 10/2008 | Brister et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262330 A1 | 10/2008 | Reynolds et al. |
| 2008/0262469 A1 | 10/2008 | Brister et al. |
| 2008/0269673 A1 | 10/2008 | Butoi |
| 2008/0269723 A1 | 10/2008 | Mastrototaro et al. |
| 2008/0275313 A1 | 11/2008 | Brister et al. |
| 2008/0281167 A1 | 11/2008 | Soderberg et al. |
| 2008/0283396 A1 | 11/2008 | Wang |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2009/0005659 A1 | 1/2009 | Kollias et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006133 A1 | 1/2009 | Weinert et al. |
| 2009/0007237 A1 | 1/2009 | Lorsch |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0018779 A1 | 1/2009 | Cohen et al. |
| 2009/0030294 A1 | 1/2009 | Petisce et al. |
| 2009/0030733 A1 | 1/2009 | Cohen et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0036915 A1 | 2/2009 | Karbowniczek et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048501 A1 | 2/2009 | Goodnow |
| 2009/0048503 A1 | 2/2009 | Dalal et al. |
| 2009/0054866 A1 | 2/2009 | Teisen-Simony et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0069658 A1 | 3/2009 | Say |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088427 A1 | 4/2009 | Clickman et al. |
| 2009/0088614 A1 | 4/2009 | Taub |
| 2009/0088787 A1 | 4/2009 | Koike et al. |
| 2009/0099436 A1 | 4/2009 | Brister et al. |
| 2009/0102678 A1 | 4/2009 | Mazza |
| 2009/0105554 A1 | 4/2009 | Stahman et al. |
| 2009/0105560 A1 | 4/2009 | Solomon |
| 2009/0105569 A1 | 4/2009 | Stafford |
| 2009/0105636 A1 | 4/2009 | Hayter et al. |
| 2009/0112478 A1 | 4/2009 | Mueller, Jr. et al. |

(56) References Cited

U.S. PATENT DOCUMENTS

| | | |
|---|---|---|
| 2009/0124877 A1 | 5/2009 | Shariati et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149717 A1 | 6/2009 | Brauer et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0171182 A1 | 7/2009 | Stafford |
| 2009/0178459 A1 | 7/2009 | Li et al. |
| 2009/0182217 A1 | 7/2009 | Li et al. |
| 2009/0187351 A1 | 7/2009 | Orr et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0198215 A1 | 8/2009 | Chong et al. |
| 2009/0203981 A1 | 8/2009 | Brauker et al. |
| 2009/0204341 A1 | 8/2009 | Brauker et al. |
| 2009/0212766 A1 | 8/2009 | Olson et al. |
| 2009/0216103 A1* | 8/2009 | Brister .............. A61B 5/14517 |
| | | 600/347 |
| 2009/0221880 A1 | 9/2009 | Soderberg et al. |
| 2009/0224773 A1 | 9/2009 | Joy et al. |
| 2009/0224837 A1 | 9/2009 | Joy et al. |
| 2009/0227876 A1 | 9/2009 | Tran et al. |
| 2009/0227877 A1 | 9/2009 | Tran et al. |
| 2009/0228304 A1 | 9/2009 | Ciarniello et al. |
| 2009/0234200 A1 | 9/2009 | Husheer |
| 2009/0240120 A1 | 9/2009 | Mensinger et al. |
| 2009/0240127 A1 | 9/2009 | Ray |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247931 A1 | 10/2009 | Damgaard-Sorensen |
| 2009/0253973 A1 | 10/2009 | Bashan et al. |
| 2009/0258790 A1 | 10/2009 | Cohen et al. |
| 2009/0259118 A1 | 10/2009 | Feldman et al. |
| 2009/0267765 A1 | 10/2009 | Greene et al. |
| 2009/0269315 A1 | 10/2009 | Fraser et al. |
| 2009/0270765 A1 | 10/2009 | Ghesquire et al. |
| 2009/0273353 A1 | 11/2009 | Kroh et al. |
| 2009/0278553 A1 | 11/2009 | Kroh et al. |
| 2009/0281519 A1 | 11/2009 | Rao et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0292184 A1 | 11/2009 | Funderburk et al. |
| 2009/0292185 A1 | 11/2009 | Funderburk et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299167 A1 | 12/2009 | Seymour |
| 2009/0299276 A1 | 12/2009 | Brauker et al. |
| 2010/0004597 A1 | 1/2010 | Gryn et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049014 A1 | 2/2010 | Funderburk et al. |
| 2010/0049024 A1 | 2/2010 | Saint et al. |
| 2010/0063373 A1 | 3/2010 | Kamath et al. |
| 2010/0069728 A1 | 3/2010 | Funderburk et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0088199 A1 | 4/2010 | Tipirneni |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100113 A1 | 4/2010 | Iio et al. |
| 2010/0105999 A1 | 4/2010 | Dixon et al. |
| 2010/0113897 A1 | 5/2010 | Brenneman et al. |
| 2010/0119693 A1 | 5/2010 | Tapsak et al. |
| 2010/0121169 A1 | 5/2010 | Petisce et al. |
| 2010/0146300 A1 | 6/2010 | Brown |
| 2010/0152554 A1 | 6/2010 | Steine et al. |
| 2010/0160759 A1 | 6/2010 | Celentano et al. |
| 2010/0160760 A1 | 6/2010 | Shults et al. |
| 2010/0161240 A1 | 6/2010 | Tseng et al. |
| 2010/0161269 A1 | 6/2010 | Kamath et al. |
| 2010/0168538 A1 | 7/2010 | Keenan et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168546 A1 | 7/2010 | Kamath et al. |
| 2010/0168547 A1 | 7/2010 | Kamath et al. |
| 2010/0168645 A1 | 7/2010 | Kamath et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0179399 A1 | 7/2010 | Goode et al. |
| 2010/0179400 A1 | 7/2010 | Brauker et al. |
| 2010/0179401 A1 | 7/2010 | Rasdal et al. |
| 2010/0179402 A1 | 7/2010 | Goode et al. |
| 2010/0179404 A1 | 7/2010 | Kamath et al. |
| 2010/0179405 A1 | 7/2010 | Goode et al. |
| 2010/0179407 A1 | 7/2010 | Goode et al. |
| 2010/0179408 A1 | 7/2010 | Kamath et al. |
| 2010/0179409 A1 | 7/2010 | Kamath et al. |
| 2010/0185065 A1 | 7/2010 | Goode et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode et al. |
| 2010/0185073 A1 | 7/2010 | Goode et al. |
| 2010/0185074 A1 | 7/2010 | Goode et al. |
| 2010/0185075 A1 | 7/2010 | Brister et al. |
| 2010/0190435 A1 | 7/2010 | Cook et al. |
| 2010/0191082 A1 | 7/2010 | Brister et al. |
| 2010/0198033 A1 | 8/2010 | Krulevitch et al. |
| 2010/0198034 A1 | 8/2010 | Thomas et al. |

(56) References Cited

U.S. PATENT DOCUMENTS

| | | | |
|---|---|---|---|
| 2010/0198035 | A1 | 8/2010 | Kamath et al. |
| 2010/0198036 | A1 | 8/2010 | Kamath et al. |
| 2010/0198142 | A1 | 8/2010 | Sloan et al. |
| 2010/0204653 | A1 | 8/2010 | Gryn et al. |
| 2010/0212583 | A1 | 8/2010 | Brister et al. |
| 2010/0214104 | A1 | 8/2010 | Goode et al. |
| 2010/0217105 | A1 | 8/2010 | Yodfat et al. |
| 2010/0217557 | A1 | 8/2010 | Kamath et al. |
| 2010/0223013 | A1 | 9/2010 | Kamath et al. |
| 2010/0223022 | A1 | 9/2010 | Kamath et al. |
| 2010/0223023 | A1 | 9/2010 | Kamath et al. |
| 2010/0228109 | A1 | 9/2010 | Kamath et al. |
| 2010/0228497 | A1 | 9/2010 | Kamath et al. |
| 2010/0240975 | A1 | 9/2010 | Goode et al. |
| 2010/0240976 | A1 | 9/2010 | Goode et al. |
| 2010/0261987 | A1 | 10/2010 | Kamath et al. |
| 2010/0262201 | A1 | 10/2010 | He et al. |
| 2010/0274107 | A1 | 10/2010 | Boock et al. |
| 2010/0280341 | A1 | 11/2010 | Boock et al. |
| 2010/0286496 | A1 | 11/2010 | Simpson et al. |
| 2010/0298684 | A1 | 11/2010 | Leach et al. |
| 2010/0312176 | A1 | 12/2010 | Lauer et al. |
| 2010/0324392 | A1 | 12/2010 | Yee et al. |
| 2010/0324403 | A1 | 12/2010 | Brister et al. |
| 2010/0331642 | A1 | 12/2010 | Bruce et al. |
| 2010/0331644 | A1 | 12/2010 | Neale et al. |
| 2010/0331648 | A1 | 12/2010 | Kamath et al. |
| 2010/0331653 | A1 | 12/2010 | Stafford |
| 2010/0331656 | A1 | 12/2010 | Mensinger et al. |
| 2010/0331657 | A1 | 12/2010 | Mensinger et al. |
| 2011/0004085 | A1 | 1/2011 | Mensinger et al. |
| 2011/0004276 | A1 | 1/2011 | Blair et al. |
| 2011/0009727 | A1 | 1/2011 | Mensinger et al. |
| 2011/0024043 | A1 | 2/2011 | Boock et al. |
| 2011/0024307 | A1 | 2/2011 | Simpson et al. |
| 2011/0027127 | A1 | 2/2011 | Simpson et al. |
| 2011/0027453 | A1 | 2/2011 | Boock et al. |
| 2011/0027458 | A1 | 2/2011 | Boock et al. |
| 2011/0028815 | A1 | 2/2011 | Simpson et al. |
| 2011/0028816 | A1 | 2/2011 | Simpson et al. |
| 2011/0040256 | A1 | 2/2011 | Bobroff et al. |
| 2011/0040263 | A1 | 2/2011 | Hordum et al. |
| 2011/0046467 | A1 | 2/2011 | Simpson et al. |
| 2011/0046977 | A1 | 2/2011 | Goodnow et al. |
| 2011/0054275 | A1 | 3/2011 | Stafford |
| 2011/0060196 | A1 | 3/2011 | Stafford |
| 2011/0073475 | A1 | 3/2011 | Kastanos et al. |
| 2011/0077490 | A1 | 3/2011 | Simpson et al. |
| 2011/0082484 | A1 | 4/2011 | Saravia et al. |
| 2011/0106126 | A1 | 5/2011 | Love et al. |
| 2011/0118579 | A1 | 5/2011 | Goode et al. |
| 2011/0118580 | A1 | 5/2011 | Goode et al. |
| 2011/0124992 | A1 | 5/2011 | Brauker et al. |
| 2011/0124997 | A1 | 5/2011 | Goode et al. |
| 2011/0125410 | A1 | 5/2011 | Goode et al. |
| 2011/0130970 | A1 | 6/2011 | Goode et al. |
| 2011/0130971 | A1 | 6/2011 | Goode et al. |
| 2011/0130998 | A1 | 6/2011 | Goode et al. |
| 2011/0137257 | A1 | 6/2011 | Gyrn et al. |
| 2011/0144465 | A1 | 6/2011 | Shults et al. |
| 2011/0145172 | A1 | 6/2011 | Petisce et al. |
| 2011/0148905 | A1 | 6/2011 | Simmons et al. |
| 2011/0152637 | A1 | 6/2011 | Kateraas et al. |
| 2011/0178378 | A1 | 7/2011 | Brister et al. |
| 2011/0178461 | A1 | 7/2011 | Chong et al. |
| 2011/0184258 | A1 | 7/2011 | Stafford |
| 2011/0190603 | A1 | 8/2011 | Stafford |
| 2011/0190614 | A1 | 8/2011 | Brister et al. |
| 2011/0201910 | A1 | 8/2011 | Rasdal et al. |
| 2011/0201911 | A1 | 8/2011 | Johnson et al. |
| 2011/0218414 | A1 | 9/2011 | Kamath et al. |
| 2011/0231107 | A1 | 9/2011 | Brauker et al. |
| 2011/0231140 | A1 | 9/2011 | Goode et al. |
| 2011/0231141 | A1 | 9/2011 | Goode et al. |
| 2011/0231142 | A1 | 9/2011 | Goode et al. |
| 2011/0253533 | A1 | 10/2011 | Shults et al. |
| 2011/0257895 | A1 | 10/2011 | Brauker et al. |
| 2011/0263958 | A1 | 10/2011 | Brauker et al. |
| 2011/0270062 | A1 | 11/2011 | Goode et al. |
| 2011/0270158 | A1 | 11/2011 | Brauker et al. |
| 2011/0275919 | A1 | 11/2011 | Petisce et al. |
| 2011/0288574 | A1 | 11/2011 | Curry et al. |
| 2011/0290645 | A1 | 12/2011 | Brister et al. |
| 2011/0313543 | A1 | 12/2011 | Brauker et al. |
| 2011/0319729 | A1 | 12/2011 | Donnay et al. |
| 2011/0319733 | A1 | 12/2011 | Stafford |
| 2011/0319738 | A1 | 12/2011 | Woodruff et al. |
| 2011/0319739 | A1 | 12/2011 | Kamath et al. |
| 2011/0320130 | A1 | 12/2011 | Valdes et al. |
| 2012/0010642 | A1 | 1/2012 | Lee et al. |
| 2012/0035445 | A1 | 2/2012 | Boock et al. |
| 2012/0040101 | A1 | 2/2012 | Tapsak et al. |
| 2012/0046534 | A1 | 2/2012 | Simpson et al. |
| 2012/0078071 | A1 | 3/2012 | Bohm et al. |
| 2012/0108934 | A1 | 5/2012 | Valdes et al. |
| 2012/0108983 | A1 | 5/2012 | Banet et al. |
| 2012/0190989 | A1 | 7/2012 | Kaiser et al. |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1177802 | 2/2002 |
| EP | 0987982 | 1/2007 |
| EP | 2060284 | 5/2009 |
| EP | 2201969 | 6/2010 |
| EP | 2327362 | 6/2011 |
| EP | 2335587 | 6/2011 |
| JP | 11-506629 | 6/1999 |
| JP | 2003-527138 | 9/2003 |
| JP | 2004-520103 | 7/2004 |
| JP | 2004-520898 | 7/2004 |
| JP | 2006-517804 | 8/2006 |
| WO | WO-1996/039977 | 5/1996 |
| WO | WO-1996/025089 | 8/1996 |
| WO | WO-1996/035370 | 11/1996 |
| WO | WO-1997/021457 | 6/1997 |
| WO | WO-1998/035053 | 8/1998 |
| WO | WO-1998/056293 | 12/1998 |
| WO | WO-1999/033504 | 7/1999 |
| WO | WO-1999/056613 | 11/1999 |
| WO | WO-2000/049940 | 8/2000 |
| WO | WO-2000/059370 | 10/2000 |
| WO | WO-2000/072181 | 11/2000 |
| WO | WO-2000/075814 | 12/2000 |
| WO | WO-2000/078992 | 12/2000 |
| WO | WO-2001/052935 | 7/2001 |
| WO | WO-2001/054753 | 8/2001 |
| WO | WO-2002/016905 | 2/2002 |
| WO | WO-2002/050534 | 6/2002 |
| WO | WO-2002/058537 | 8/2002 |
| WO | WO-2003/028784 | 4/2003 |
| WO | WO-2003/041231 | 5/2003 |
| WO | WO-2003/049597 | 6/2003 |
| WO | WO-2003/073936 | 9/2003 |
| WO | WO-2003/076893 | 9/2003 |
| WO | WO-2003/082091 | 10/2003 |
| WO | WO-2004/054445 | 7/2004 |
| WO | WO-2004/060436 | 7/2004 |
| WO | WO-2004/061420 | 7/2004 |
| WO | WO-2004/110256 | 12/2004 |
| WO | WO-2005/040793 | 5/2005 |
| WO | WO-2005/045744 | 5/2005 |
| WO | WO-2005/084534 | 9/2005 |
| WO | WO-2005/089103 | 9/2005 |
| WO | WO-2005/119524 | 12/2005 |
| WO | WO-2006/026741 | 3/2006 |
| WO | WO-2006/032653 | 3/2006 |
| WO | WO-2006/042811 | 4/2006 |

(56)                    References Cited

FOREIGN PATENT DOCUMENTS

WO        WO-2006/069657        7/2006
WO        WO-2006/086423        8/2006
WO        WO-2006/108809        10/2006
WO        WO-2006/124099        11/2006
WO        WO-2007/041069        4/2007
WO        WO-2007/140783        12/2007
WO        WO-2007/143225        12/2007
WO        WO-2008/001366        1/2008
WO        WO-2008065646         6/2008
WO        WO-2008133702         11/2008
WO        WO-2009/062675        5/2009
WO        WO-20100112521        10/2010
WO        WO-2011/002815        1/2011
WO        WO-2011/022418        2/2011

OTHER PUBLICATIONS

Amour, J.C. et al., "Application of Chronic Intravascular Blood Glucose Sensor in Dogs," Diabetes, vol. 39, 1990, pp. 1519-1526.

Bennion, N. et al., "Alternate Site Glucose Testing: A Crossover Design," Diabetes Technology & Therapeutics, vol. 4, No. 1, 2002, pp. 25-33.

Bendt, D. J., et al., "Introduction to the Minitrack: Databases, Data Warehousing, and Data Mining in Health Care," System Sciences, Proceedings of 33rd Annual Hawaii Intenrational Conference, Jan. 4-7, 2000, pp. 1588.

Bindra, D.S. et al., "Design and in Vitro Studies of a Needle-Type Glucose Sensor for Subcutaneous Monitoring," Anal. Chem., 63(17):1692-1696 (Sep. 1, 1991).

Blank, T.B. et al., "Clinical Results from a Non-Invasive Blood Glucose Monitor," Optical Diagnostics and Sensing of Biological Fluids and Glucose and Cholesterol Monitoring II, Proceedings of SPIE, vol. 4624, 2002, pp. 1-10.

Bobbioni-Harsch, E. et al., "Lifespan of subcutaneous glucose sensors and their performances during dynamic glycaemia changes in rats," J. Biomed. Eng. 15:457-463 (1993).

Brooks, S.L. et al., "Development of an On-Line Glucose Sensor for Fermentation Monitoring," Biosensors, vol. 3, 1987/88, pp. 45-56.

Bühling et al., Journal of Perinatal Medicine, 2005, vol. 33, pp. 125-131.

Cass, A.E. et al., "Ferrocene-Medicated Enzyme Electrode for Amperometric Determination of Glucose," Analytical Chemistry, vol. 56, No. 4, 1984, pp. 667-671.

Cheyne, E.H. et al., "Performance of a Continuous Glucose Monitoring System During Controlled Hypoglycaemia in Healthy Volunteers," Diabetes Technology & Therapeutics, vol. 4, No. 5, 2002, pp. 607-613.

Csoegi, E. et al., "Design and Optimization of a Selective Subcutaneously Implantable Glucose Electrode Based on 'Wired' Glucose Oxidase," Analytical Chemistry, vol. 67, No. 7, 1995, pp. 1240-1244.

Cullen, M.T., et al., "The Changing Presentations of Diabetic Ketoacidosis During Pregnancy," Amer. J. Perinatol, 1996, vol. 13, No. 7, pp. 449-451 (abstract only).

Feldman, B. et al., "A Continuous Glucose Sensor Based on Wired Enzyme™ Technology—Results from a 3-Day Trial in Patients with Type 1 Diabetes," Diabetes Technology & Therapeutics, vol. 5, No. 5, 2003, pp. 769-779.

Feldman, B. et al., "Correlation of Glucose Concentrations in Interstitial Fluid and Venous Blood During Periods of Rapid Glucose Change," Abbott Diabetes Case, Inc. Freestyle Navigator Continuous Glucose Monitor Pamphlet, 2004.

Gunasingham, et al., "Electrochemically Modulated Optrode for Glucose," Biosensors & Bioelectronics, vol. 7, 1992, pp. 353-359.

Gregg, B. A. et al., "Cross-Linked Redox Gels Containing Glucose Oxidase for Amperometric Biosensor Applications," Analytical Chemistry, 62(3):258-263 (Feb. 1, 1990).

Harrison, D.J. et al., "Characterization of Perfluorosulfonic Acid Polymer Coated Enzyme Electrodes and a Miniaturized Integrated Potentiostat for Glucose Analysis in Whole Blood," Anal. Chem., 60 (19):2002-2007 (Oct. 1, 1988).

Heller, A., "Electrical Connection of Enzyme Redox Centers to Electrodes," J. Phys. Chem., 96 (9):3579-3587 (1992).

Heller, A., "Electrical Wiring of Redox Enzymes," Acc. Chem. Res., 23(5):129-134 (1990).

Ikeda, T., et al., "Artificial Pancreas—Investigation of the Stability of Glucose Sensors Using a Telemetry System" (English language translation of abstract), Jpn. J. Artif. Organs, vol. 19, No. 2, 1990, 889-892.

Isermann, R., "Supervision, Fault-Detection and Fault-Diagnosis Methods—An Introduction", Control Engineering Practice, vol. 5, No. 5, 1997, pp. 639-652.

Isermann, R. et al., "Trends in the Application of Model-Based Fault Detection and Diagnosis of Technical Processes", Control Engineering Practice, vol. 5, No. 5, 1997, pp. 709-719.

Johnson, K., et al., "In vivo evaluation of an electroenzymatic glucose sensor implanted in subcutaneous tissue," Biosensors and Bioelectronics, 1992, vol. 7, pp. 709-714.

Johnson, P.C., "Peripheral Circulation," John Wiley & Sons, 1978, pp. 198.

Jovanovic, Diabetes Technology & Therapeutics, 2000, vol. 2, Supplement 1, pp. S-67-71.

Jungheim, K. et al., "How Rapid Does Glucose Concentration Change in Daily Life of Patients with Type 1 Diabetes?", 2002, pp. 250.

Jungheim, K. et al., "Risky Delay of Hypoglycemia Detection by Glucose Monitoring at the Arm", Diabetes Care, vol. 24, No. 7, 2001, pp. 1303-1304.

Kaplan, S. M., "Wiley Electrical and Electronics Engineering Dictionary", IEEE Press, 2004, pp. 141, 142, 548, 549.

Lodwig, V. et al., "Continuous Glucose Monitoring with Glucose Sensors: Calibration and Assessment Criteria," Diabetes Technology & Therapeutics, vol. 5, No. 4, 2003, pp. 573-587.

Lortz, J. et al., "What is Bluetooth? We Explain the Newest Short-Range Connectivity Technology", Smart Computing Learning Series, Wireless Computing, vol. 8, Issue 5, 2002, pp. 72-74.

Maidan, R. et al., "Elimination of Electroaxidizable Interferant-Produced Currents in Amperometric Biosensors," Analytical Chemistry, 64(23):2889-2896 (Dec. 1, 1992).

Malin, S.F. et al., "Noninvasive Prediction of Glucose by Near-Infrared Diffuse Reflectance Spectoscopy," Clinical Chemistry, vol. 45, No. 9, 1999, pp. 1651-1658.

Mastrototaro, J.J. et al., "An Electroenzymatic Glucose Sensor Fabricated on a Flexible Substrate," Sensors and Biosensors B Chemical, B5:139-144 (1991).

McGarraugh, G. et al., "Glucose Measurements Using Blood Extracted from the Forearm and the Finger," TheraSense, Inc., 2001, 16 pages.

McGarraugh, G. et al., "Physiological Influences on Off-Finger Glucose Testing," Diabetes Technology & Therapeutics, vol. 3, No. 3, 2001, pp. 367-376.

McKean, B. D. et al., "A Telemetry-Instrumentation System for Chronically Implanted Glucose and Oxygen Sensors", IEEE Transactions on Biomedical Engineering, vol. 35, No. 7, 1988, pp. 526-532.

Minimed Technologies, "Tape Tips and Other Infusion Site Information," 1995.

Moatti-Sirat, D. et al., "Towards continuous glucose monitoring: in vivo evaluation of a miniaturized glucose sensor implanted for several days in rat subcutaneous tissue," Diabetolocia, 35(3) (1 page—Abstract only) (Mar. 1992).

Morbiducci, U. et al., "Improved Usability of the Minimal Model of Insulin Sensitivity Based on an Automated Approach and Genetic algorithms for Parameter Estimation," Clinical Science, vol. 112, 2007, pp. 257-263.

Mougiakakou et al., "A Real Time Simulation Model of Glucose-Insulin Metabolism for Type 1 Diabetes Patients," Proceedings of the 2005 IEEE, 2005, pp. 298-301.

Ohara, T. J. et al., "Glucose Electrodes Based on Cross-Linked [Os(bpy).sub.2 Cl].sup. +/2+ Complexed Poly(I-vinylimadazole) Films," Analytical Chemistry, 65(23):3512-3516 (Dec. 1, 1993).

(56)                    References Cited

OTHER PUBLICATIONS

Opinion of the Court, Supreme Court of the United States, No. 04-1350, *KSR International co.*, Petitioner v. *Teleflex Inc.* et al., Apr. 30, 2007.

Pickup, J. et al., "Implantable Glucose Sensors: Choosing the Appropriate Sensing Strategy," Biosensors, vol. 3, 1987/88, pp. 335-346.

Pickup, J. et al., "In Vivo Molecular Sensing in Diabetes Mellitus: An Implantable Glucose Sensor with Direct Electron Transfer," Diabetologia, vol. 32, 1989, pp. 213-217.

Parker, R. et al., "Robust H∞ Glucose Control in Diabetes Using a Physiological Model," AIChE Journal, vol. 46, No. 12, 2000, pp. 2537-2549.

Pishko, M.V. et al., "Amperometric Glucose Microelectrodes Prepared Through Immobilization of Glucose Oxidase in Redox Hydrogels," Analytical Chemistry, vol. 63, No. 20, 1991, pp. 2268-2272.

Poitout, V. et al., "In vitro and in vivo evaluation in dogs of a miniaturized glucose sensor," ASAIO Transactions, 37(3) (1 page—Abstract only) (Jul.-Sep. 1991).

Quinn, C.P. et al., Kinetics of Glucose Delivery to Subcutaneous Tissue in Rats Measured with 0.3-mm Amperometric Microsensors, The American Physiological Society, 1995, E155-E161.

Reach, G. et al., "Can Continuous Glucose Monitoring Be Used for the Treatment of Diabetes?" Analytical Chemistry, 64(6):381-386 (Mar. 15, 1992).

Rebrin, K. et al., "Automated Feedback Control of Subcutaneous Glucose Concentration in Diabetic Dogs," Diabetologia, 32(8):573-576 (Aug. 1989).

Roe, J.N. et al., "Bloodless Glucose Measurements," Critical Review in Therapeutic Drug Carrier Systems, vol. 15, Issue 3, 1998, pp. 199-241.

Sakakida, M. et al., "Development of Ferrocene-Mediated Needle-Type Glucose Sensor as a Measure of True Subcutaneous Tissue Glucose Concentration," Artificial Organs Today, vol. 2, No. 2, 1992, pp. 145-158.

Sakakida, M. et al., "Ferrocene-Medicated Needle-Type Glucose Sensor Covered with Newly Designed Biocompatible Membrane," Sensors and Actuators B, vol. 13-14, 1993, pp. 319-322.

Salehi, C. et al., "A Telemetry-Instrumentation System for Long-Term Implantable Glucose and Oxygen Sensors", Analytical Letters, vol. 29, No. 13, 1996, pp. 2289-2308.

Schmidt, F. J., et al., "Calibration of a Wearable Glucose Sensor", The International Journal of Artificial Organs, vol. 15, No. 1, 1992, pp. 55-61.

Schmidtke, D.W. et al., "Measurement and Modeling of the Transient Difference Between Blood and Subcutaneous Glucose Concentrations in the Rat After Injection of Insulin," Proceedings of the National Academy of Sciences, vol. 95, 1998, pp. 294-299.

Shaw, G. W. et al., "In Vitro Testing of a Simply Constructed, Highly Stable Glucose Sensor Suitable for Implantation in Diabetic Patients", Biosensors & Bioelectronics, vol. 6, 1991, pp. 401-406.

Shichiri, M. et al., "Glycaemic Control in Pancreatectomized Dogs with a Wearable Artificial Endocrine Pancreas," Diabetologia, vol. 24, 1983, pp. 179-184.

Shichiri, M. et al., "In Vivo Characteristics of Needle-Type Glucose Sensor—Measurements of Subcutaneous Glucose Concentrations in Human Volunteers," Hormone and Metabolic Research Supplement Series, vol. 20, 1988, pp. 17-20.

Shichiri, M. et al., "Membrane Design for Extending the Long-Life of an Implantable Glucose Sensor," Diabetes Nutrition and Metabolism, vol. 2, 1989, pp. 309-313.

Shichiri, M. et al., "Needle-Type Glucose Sensor for Wearable Artificial Endocrine Pancreas," Implantable Sensors for Closed-Loop Prosthetic Systems, Chapter 15, 1985, pp. 197-210.

Shichiri, M. et al., "Telemetry Glucose Monitoring Device with Needle-Type Glucose Sensor: A Useful Tool for Blood Glucose Monitoring in Diabetic Individuals", Diabetes Care, vol. 9, No. 3, 1986, pp. 298-301.

Shichiri, M. et al., "Wearable Artificial Endocrine Pancreas with Needle-Type Glucose Sensor," The Lancet, 1982, pp. 1129-1131.

Shults, M. C. et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.

Sternberg, R. et al., "Study and Development of Multilayer Needle-Type Enzyme-Based Glucose Microsensors," Biosensors, vol. 4, 1988, pp. 27-40.

Thompson, M. et al., "In Vivo Probes: Problems and Perspectives," Clinical Biochemistry, vol. 19, 1986, pp. 255-261.

Travenol Laboratories, Inc., An Introduction of "Eugly," Book 1, 1985, pp. 1-22.

Turner, A. et al., "Diabetes Mellitus: Biosensors for Research and Management," Biosensors, vol. 1, 1985, pp. 85-115.

Updike, S. J. et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117-137.

Velho, G. et al., "Strategies for Calibrating a Subcutaneous Glucose Sensor", Biomedica Biochimica Acta, vol. 48, 1989, pp. 957-964.

Wang et al., Journal of the Shanghai Medical University, 2000, vol. 27, pp. 393-395 (Abstract).

Wilson, G.S. et al., "Progress Toward the Development of an Implantable Sensor for Glucose," Clinical Chemistry, vol. 38, No. 9, 1992, pp. 1613-1617.

Ye, L. et al., "High Current Density "Wired" Quinoprotein Glucose Dehydrogenase Electroade," Anal. Chem., 65(3):238-241 (Feb. 1, 1993).

Canadian Patent Application No. CA-2,752,455, Examiner's Report mailed Jun. 13, 2012.

Canadian Patent Application No. CA-2,858,901, Examiner's Report mailed Jan. 25, 2016.

Chinese Patent Application No. 200880005149.1, Notification of Granting a Patent Right for an Invention mailed Jun. 21, 2013.

Chinese Patent Application No. 200880005149.1, Original Language and English Translation of Office Action mailed Aug. 17, 2011.

Chinese Patent Application No. 200880005149.1, Original Language and English Translation of Office Action mailed Dec. 3, 2012.

Chinese Patent Application No. 200880005149.1, Original Language and English Translation of Office Action mailed Feb. 16, 2012.

Chinese Patent Application No. 200880005149.1, Original Language and English Translation of Office Action mailed Jul. 29, 2010.

European Patent Application No. EP-05756627.5, Supplementary European Search Report mailed Dec. 4, 2009.

European Patent Application No. EP-05756627.5, Office Action mailed Jun. 24, 200. Patent Application No. EP-05756627.5, Decision to Refuse the Application mailed Dec. 12, 2013.

European Patent Application No. EP-05756627.5, Decision to Refuse the Application mailed Dec. 12, 2013.

European Patent Application No. EP-05756627.5, Decision to Refuse the Application mailed Dec. 7, 2012.

European Patent Application No. EP-05756627.5, Examination Report mailed Jun. 7, 2013.

European Patent Application No. EP-05756627.5, Official Communication mailed Jun. 13, 2012.

PCT Application No. PCT/US2005/020044, International Preliminary Report on Patentability mailed Dec. 20, 2006.

PCT Application No. PCT/US2008/054165, International Preliminary Report on Patentability and Written Opinion of the International Searching Authority mailed Aug. 27, 2009.

PCT Application No. PCT/US2008/054165, International Search Report and Written Opinion of the International Searching Authority mailed Jun. 5, 2008.

PCT Application No. PCT/US2008/067791, International Search Report and Written Opinion of the International Searching Authority mailed Sep. 29, 2008.

PCT Application No. PCT/US2008/067791, International Search Report on Patentability and Written Opinion of the International Searching Authority mailed Jan. 7, 2010.

(56)             References Cited

OTHER PUBLICATIONS

PCT Application No. PCT/US2010/022860, International Search Report and Written Opinion mailed Mar. 23, 2010.
PCT Application No. PCT/US2010/022860, International Preliminary Report on Patentability and Written Opinion of the International Searching Authority mailed Aug. 18, 2011.
PCT Application No. PCT/US2010/047381, International Search Report and Written Opinion mailed Oct. 15, 2010.
PCT Application No. PCT/US2010/047381, International Preliminary Report on Patentability and Written Opinion of the International Searching Authority mailed Mar. 15, 2012.
PCT Application No. PCT/US2010/050772, International Search Report and Written Opinion mailed Dec. 3, 2010.
PCT Application No. PCT/US2010/050772, International Preliminary Report on Patentability and Written Opinion of the International Searching Authority mailed Apr. 12, 2012.
PCT Application No. PCT/US2010/050888, International Search Report and Written Opinion mailed Nov. 29, 2010.
PCT Application No. PCT/US2010/050888, International Preliminary Report on Patentability and Written Opinion of the International Searching Authority mailed Apr. 12, 2012.
PCT Application No. PCT/US2010/051861, International Search Report and Written Opinion mailed Nov. 30, 2010.
PCT Application No. PCT/US2010/051861, International Preliminary Report on Patentability and Written Opinion of the International Searching Authority mailed Apr. 19, 2012.
Russian Patent Application No. 2009134334, Original Language and English Translation of Office Action mailed Feb. 7, 2012.
U.S. Appl. No. 12/893,974, Office Action mailed Mar. 28, 2013.
U.S. Appl. No. 90/008,457, Request for Reexamination of U.S. Pat. No. 6,990,366, filed Jan. 23, 2007.
U.S. Appl. No. 90/009,328 & U.S. Appl. No. 90/009,328, Notice of Intent to Issue Reexamination Certificate mailed Nov. 20, 2009.
U.S. Appl. No. 90/009,328 & U.S. Appl. No. 90/009,328, Office Action mailed Aug. 4, 2009.
U.S. Appl. No. 90/009,328 & U.S. Appl. No. 90/009,328, Office Action mailed Sep. 30, 2009.

U.S. Appl. No. 90/009,104, Office Action mailed Oct. 16, 2008.
U.S. Appl. No. 90/009,104, Order Granting Request for Reexamination mailed Jun. 5, 2008.
U.S. Appl. No. 90/009,104, Request for Reexamination of U.S. Pat. No. 6,990,366 filed Apr. 8, 2008.
U.S. Appl. No. 90/009,328, Order Granting Request for Reexamination mailed Dec. 9, 2008.
U.S. Appl. No. 90/009,328, Request for Reexamination of U.S. Pat. No. 6,990,366 filed Nov. 10, 2008.
U.S. Appl. No. 90/010,791, Notice of Intent to Issue Reexamination Certificate mailed May 17, 2011.
U.S. Appl. No. 90/010,791, Office Action mailed Dec. 17, 2010.
U.S. Appl. No. 90/010,791, Office Action mailed May 28, 2010.
U.S. Appl. No. 90/010,791, Order Granting Request for Reexamination mailed Feb. 22, 2010.
U.S. Appl. No. 90/010,791, Request for Reexamination of U.S. Pat. No. 6,990,366 filed Dec. 22, 2009.
U.S. Appl. No. 90/011,730, Notice of Intent to Issue Reexam Certificate for U.S. Pat. No. 6,990,366 mailed Apr. 5, 2012.
U.S. Appl. No. 90/011,730, Office Action mailed Jan. 11, 2012.
U.S. Appl. No. 90/011,730, Order Granting Request for Reexamination of U.S. Pat. No. 6,990,366 mailed Aug. 24, 2011.
U.S. Appl. No. 90/011,730, Request for Reexamination of U.S. Pat. No. 6,990,366 filed Jun. 3, 2011.
U.S. Appl. No. 95/002,113, Order Denying Request for Reexamination of U.S. Pat. No. 6,990,366 mailed Nov. 13, 2012.
U.S. Appl. No. 95/002,113, Petition for Review of the Order Denying Request Reexamination of U.S. Pat. No. 6,990,366 mailed Dec. 13, 2012.
U.S. Appl. No. 95/002,113, Request for Reexamination of U.S. Pat. No. 6,990,366 filed Aug. 30, 2012.
U.S. Appl. No. 95/002,162, Order Denying Request for Reexamination of U.S. Pat. No. 8,175,673 mailed Nov. 13, 2012.
U.S. Appl. No. 95/002,162, Petition for Review of the Order Denying Request Reexamination of U.S. Pat. No. 8,175,673 mailed Dec. 13, 2012.
U.S. Appl. No. 95/002,162, Request for Reexamination of U.S. Pat. No. 8,175,673 filed Sep. 7, 2012.

* cited by examiner

Windowed Leads

SMT Assembly

INTERCONNECT FOR ON-BODY ANALYTE MONITORING DEVICE

RELATED APPLICATIONS

The present application is a continuation of U.S. patent application Ser. No. 17/137,785, filed Dec. 30, 2020, which is a continuation of U.S. patent application Ser. No. 16/941, 717, filed Jul. 29, 2020, now abandoned, which is a continuation of U.S. patent application Ser. No. 15/674,439, filed Aug. 10, 2017, now U.S. Pat. No. 10,765,351, which is a continuation of U.S. patent application Ser. No. 15/140, 309, filed Apr. 27, 2016, now U.S. Pat. No. 9,750,444, which is a continuation of U.S. patent application Ser. No. 12/895, 015, filed Sep. 30, 2010, now U.S. Pat. No. 9,351,669, which claims the benefit of U.S. Provisional Application No. 61/247,516, filed Sep. 30, 2009, all of which are incorporated herein by reference in their entireties for all purposes.

FIELD OF THE INVENTION

The present invention relates to an analyte monitoring system. More particularly, the present invention relates to apparatus for establishing electrical communication between an analyte sensor and an electronics unit in an on-body analyte monitoring device.

BACKGROUND OF THE INVENTION

The detection and/or monitoring of glucose levels or other analytes, such as lactate, oxygen, A1C, or the like, in certain individuals is vitally important to their health. For example, the monitoring of glucose is particularly important to individuals with diabetes. Diabetics generally monitor glucose levels to determine if their glucose levels are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including convenience, testing discretion, pain associated with glucose testing, and cost.

Devices have been developed for the automatic monitoring of analyte(s), such as glucose, in bodily fluid such as in the blood stream or in interstitial fluid ("ISF"), or other biological fluid. Some of these analyte measuring devices are configured so that at least a portion of the devices are positioned below a skin surface of a user, e.g., in a blood vessel or in the subcutaneous tissue of a user, so that the monitoring is accomplished in vivo.

With the continued development of analyte monitoring devices and systems, there is a need for such analyte monitoring devices, systems, and methods, as well as for processes for manufacturing analyte monitoring devices and systems that are cost effective, convenient, and with reduced pain, provide discreet monitoring to encourage frequent analyte monitoring to improve glycemic control.

Typically, a glucose monitor consists of an analyte sensor that is implanted in a patient and an electronics unit adapted to establish electrical communication with the analyte sensor. The electrical communication may be accomplished utilizing a number of different interconnects. For example, some electronics units utilize pogo pins, polymer pins, solid pins, or springs as interconnects. However, each of these known interconnects has potential drawbacks. For example, pogo pins are not durable, and moisture can seep into the spring mechanism, thereby degrading their performance. Similarly, polymer pins can degrade and wear after multiple cleanings Solid pins generally require extensive modification of existing systems, leading to higher costs for the patient. Spring connections are delicate, and may be prone to failure after extended use. Therefore, there clearly exists a need for a low-cost, waterproof, flexible interconnect that allows for efficient and reliable electrical communication between an analyte sensor and an electronics unit.

In other instances, a user may need to wear an on-body analyte monitoring device for an extended period of time. Generally, the on-body monitoring device includes a mounting unit housing an analyte sensor and an electronics unit. However, such devices can be bulky and uncomfortable due to the size and vertical height ("Z-height") of the electronics unit and the size of the mounting unit, which should be sufficiently large to house the electronics unit. Therefore, there exists a need for an on-body analyte monitoring device having a streamlined body and low profile (e.g., reduced Z-height) for a more comfortable wear and patient compliance.

SUMMARY OF THE INVENTION

Generally, the present invention relates to an interconnect configured to establish electrical communication between an analyte sensor and an electronics unit. The analyte sensor, interconnect, and the electronics unit define an on-body analyte monitoring device having a low profile. The on-body analyte monitoring device can be used with analyte monitoring system, such as for example, a continuous glucose monitoring system or analyte measurement system which provides analyte levels on demand. An analyte monitoring system generally includes an on-body analyte monitoring device and one or more receiver/display units. Optionally, the analyte monitoring system can further include a data processing unit, such as for example a CPU. Thus, in one embodiment, the on-body analyte monitoring device comprises an analyte sensor for measuring analyte levels, an electronics unit adapted to process the signals relating to the analyte levels generated by the analyte sensor, and an interconnect adapted to establish electrical conductivity between the electronics unit and the analyte sensor.

In one embodiment, the electronics unit includes a processor disposed within the body of the electronics unit. The processor can comprise an application specific integrated circuit (ASIC). In some embodiments, an elongate interconnect is coupled to the body of the electronics unit, such as for example the sidewall of the electronics unit proximate an analyte sensor. In some embodiments, the elongate interconnect can extend laterally from the electronics unit so as to contact an analyte sensor disposed adjacent the electronics unit.

The elongate interconnect comprises conductive material, such as, but not limited to, conductive cables, such as ribbon cables. In some embodiments, the conductive material can be embedded or etched in a flexible material, such as a flexible strip of thermoplastic material. The flexible strip may be formed from any suitable thermoplastic material. For example, the thermoplastic material includes polyimides such as Apical, Kapton, UPILEX, VTEC PI, Norton TH, polyester, mylar, and Kaptrex. However, in other embodiments, the conductive material can be encapsulated in a flexible sheath.

In some embodiments, the elongate interconnect is coupled to the electronics unit, for example, to a circuit board disposed in the body of the electronics unit, to establish electrical communication between the electronics unit and interconnect. Additionally, the elongate interconnect can establish electrical communication with an analyte sensor. In some embodiments, the elongate interconnect can include a conductive material such as a conductive contact to contact or otherwise couple to the analyte sensor, thereby establishing electrical communication between the interconnect and the analyte sensor. In some embodiments, the elongate interconnect is formed of a flexible material such that the extended length of the interconnect can collapse or otherwise deform when the electronics unit is coupled to the analyte sensor. Upon disengagement of the analyte sensor and the electronics unit, the elongate interconnect can return to its non-collapsed configuration.

The analyte sensor, for example, in some embodiments, includes a substrate having conductive material, such as one or more electrodes and one or more conductive contacts. In some embodiments, the conductive material comprises gold, which can be formed using ablation techniques (e.g., laser ablation). The analyte sensor can be configured to monitor glucose levels or any other analyte of interest, including drugs.

In some embodiments, the electronics unit may further comprise a seal disposed proximate the elongate interconnect. The seal may be an individual molded component made of low durometer silicone, rubber or some other material TPE. In some embodiments, the interconnect extends approximately 1 mm beyond the face of the seal. When the electronics unit is locked into position, the interconnect compresses and makes contact with the conductive pads on the sensor. The seal also compresses to form a barrier around the perimeter of the interconnect/sensor connection. The interconnect may work without the seal, however once liquid or dust got in, the interconnect/sensor interface may be compromised and fail.

In some embodiments, the seal includes an opening to permit direct contact of a conductive contact disposed on the interconnect to the analyte sensor. In this manner, the analyte sensor and the electronics unit can establish electrical conductivity via the closed circuit provided by the interconnect.

In another aspect of the invention, an on-body analyte monitoring device having a reduced vertical height is provided. In one embodiment, the interconnect includes a top surface and a bottom surface adapted to engage, for example, interlock, with the body of the electronics unit. The interconnect includes conductive material, which establishes electrical communication with and between both an analyte sensor and an electronics unit. In some embodiments, the electronics unit may comprise a circuit board for interfacing with a conductive area of the interconnect thereby establishing electrical communication between the interconnect and the electronics unit. Thus, when interconnect is engaged to the electronics unit, the conductive material or areas of the interconnect form a closed circuitry with the electronics unit and the analyte sensor, thereby establishing electrical communication between the analyte sensor and the electronics unit.

In some embodiments, the conductive material includes a conductive film, such as an anisotropic film or an elastomeric connector, such as a Zebra® style connector. Alternatively, the first and second conductive material can include clips.

In one embodiment, the conductive surfaces can further include an adhesive for adhering the electronics unit and analyte sensor to the interconnect. The adhesive can be a UV curable adhesive or any other suitable adhesive. Other examples include a multi-adhesive system, such as a silver loaded epoxy, which allows for the electronics unit and analyte sensor to be adhered together while also placing the electronics unit and analyte sensor in electrical communication.

The interconnect can also include a power source, such as a battery to power the electronics unit. In this manner, the electronics unit can be configured without its own internal power supply.

In some embodiments, the bottom surface of the interconnect includes an adhesive surface capable of bonding with human skin. Accordingly, the interconnect can also serve as a mounting unit to adhere the on-body device to a subject, such that a separate mounting unit component is not required.

In some embodiments, the interconnect is configured to engage the electronics unit to define a two-component on-body monitoring device. In other embodiments, the interconnect, sensor, and electronics unit are integrated to define a single component on-body monitoring device.

DETAILED DESCRIPTION OF THE EMBODIMENTS

Figure 1A:
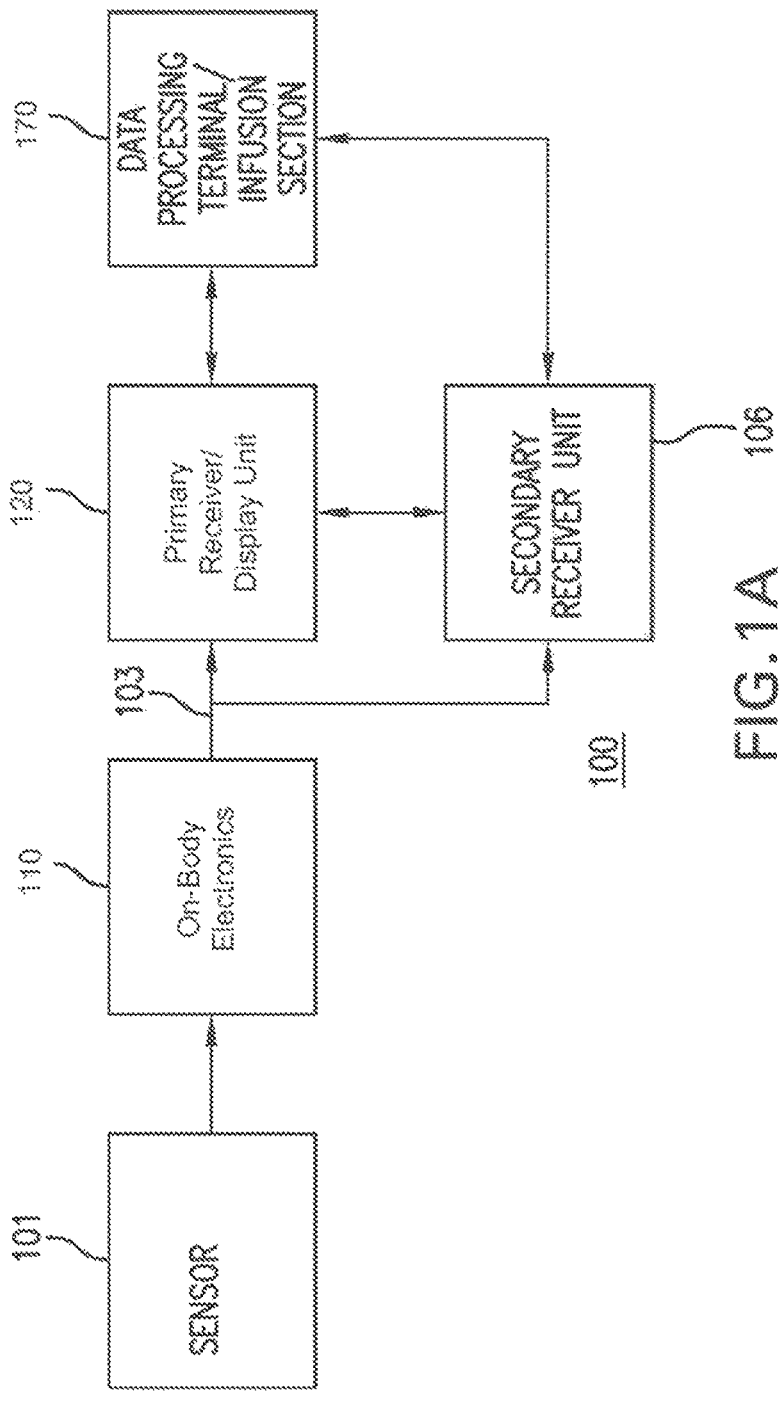
FIG. 1A illustrates a block diagram of a data monitoring and management system for practicing one or more embodiments of the present invention.

Before the present disclosure is described in detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges as also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure.

Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Generally, embodiments of the present disclosure relate to in vivo methods and devices for detecting at least one analyte such as glucose in body fluid. Accordingly, embodiments include in vivo analyte sensors configured so that at least a portion of the sensor is positioned in the body of a user (e.g., within the ISF), to obtain information about at least one analyte of the body, e.g., transcutaneously positioned in user's body. In certain embodiments, an in vivo analyte sensor is coupled to an electronics unit that is maintained on the body of the user such as on a skin surface, where such coupling provides on body, in vivo analyte sensor electronics assemblies.

In certain embodiments, analyte information is communicated from a first device such as an on body electronics unit to a second device which may include user interface features, including a display, and/or the like. Information may be communicated from the first device to the second device automatically and/or continuously when the analyte information is available, or may not be communicated automatically and/or continuously, but rather stored or logged in a memory of the first device. Accordingly, in many embodiments of the system, analyte information derived by the sensor/on body electronics (for example, on body electronics assembly) is made available in a user-usable or viewable form only when queried by the user such that the timing of data communication is selected by the user.

In this manner, analyte information is only provided or evident to a user (provided at a user interface device) when desired by the user even though an in vivo analyte sensor automatically and/or continuously monitors the analyte level in vivo, i.e., the sensor automatically monitors analyte such as glucose on a pre-defined time interval over its usage life. For example, an analyte sensor may be positioned in vivo and coupled to on body electronics for a given sensing period, e.g., about 14 days. In certain embodiments, the sensor-derived analyte information is automatically communicated from the sensor electronics assembly to a remote monitor device or display device for output to a user throughout the 14 day period according to a schedule programmed at the on body electronics (e.g., about every 1 minute or about every 5 minutes or about every 10 minutes, or the like). In certain embodiments, sensor-derived analyte information is only communicated from the sensor electronics assembly to a remote monitor device or display device at user-determined times, e.g., whenever a user decides to check analyte information. At such times, a communications system is activated, and sensor-derived information is then sent from the on body electronics to the remote device or display device.

In still other embodiments, the information may be communicated from the first device to the second device automatically and/or continuously when the analyte information is available, and the second device stores or logs the received information without presenting or outputting the information to the user. In such embodiments, the information is received by the second device from the first device when the information becomes available (e.g., when the sensor detects the analyte level according to a time schedule). However, the received information is initially stored in the second device and only output to a user interface or an output component of the second device (e.g., display) upon detection of a request for the information on the second device.

Accordingly, in certain embodiments once a sensor electronics assembly is placed on the body so that at least a portion of the in vivo sensor is in contact with bodily fluid such as ISF and the sensor is electrically coupled to the electronics unit, sensor derived analyte information may be communicated from the on body electronics to a display device on-demand by powering on the display device (or it may be continually powered), and executing a software algorithm stored in and accessed from a memory of the display device, to generate one or more request commands, control signal or data packet to send to the on body electronics. The software algorithm executed under, for example, the control of the microprocessor or application specific integrated circuit (ASIC) of the display device may include routines to detect the position of the on body electronics relative to the display device to initiate the transmission of the generated request command, control signal and/or data packet.

Display devices may also include programming stored in memory for execution by one or more microprocessors and/or ASICs to generate and transmit the one or more request command, control signal or data packet to send to the on body electronics in response to a user activation of an input mechanism on the display device such as depressing a button on the display device, triggering a soft button associated with the data communication function, and so on. The input mechanism may be alternatively or additionally provided on or in the on body electronics which may be configured for user activation. In certain embodiments, voice commands or audible signals may be used to prompt or instruct the microprocessor or ASIC to execute the software routine(s) stored in the memory to generate and transmit the one or more request command, control signal or data packet to the on body device. In the embodiments that are voice activated or responsive to voice commands or audible signals, on body electronics and/or display device includes a microphone, a speaker, and processing routines stored in the respective memories of the on body electronics and/or the display device to process the voice commands and/or audible signals. In certain embodiments, positioning the on body device and the display device within a predetermined distance (e.g., close proximity) relative to each other initiates one or more software routines stored in the memory of the display device to generate and transmit a request command, control signal or data packet.

Different types and/or forms and/or amounts of information may be sent for each on demand reading, including, but not limited to, one or more of current analyte level information (i.e., real time or the most recently obtained analyte level information temporally corresponding to the time the reading is initiated), rate of change of an analyte over a predetermined time period, rate of the rate of change of an analyte (acceleration in the rate of change), historical analyte information corresponding to analyte information obtained prior to a given reading and stored in memory of the assembly. Some or all of real time, historical, rate of change, rate of rate of change (such as acceleration or deceleration) information may be sent to a display device for a given reading. In certain embodiments, the type and/or form and/or amount of information sent to a display device may be preprogrammed and/or unchangeable (e.g., preset at manufacturing), or may not be preprogrammed and/or unchangeable so that it may be selectable and/or changeable in the field one or more times (e.g., by activating a switch of the system, etc.). Accordingly, in certain embodiments, for each on demand reading, a display device will output a current (real time) sensor-derived analyte value (e.g., in numerical format), a current rate of analyte change (e.g., in the form of an analyte rate indicator such as an arrow pointing in a direction to indicate the current rate), and analyte trend history data based on sensor readings acquired by and stored in memory of on body electronics (e.g., in the form of a graphical trace). Additionally, the on skin or sensor temperature reading or measurement associated with each on demand reading may be communicated from the on body electronics to the display device. The temperature reading or measurement, however, may not be output or displayed on the display device, but rather, used in conjunction with a software routine executed by the display device to correct or compensate the analyte measurement output to the user on the display device.

As described, embodiments include in vivo analyte sensors and on body electronics that together provide body wearable sensor electronics assemblies. In certain embodiments, in vivo analyte sensors are fully integrated with on body electronics (fixedly connected during manufacture), while in other embodiments they are separate but connectable post manufacture (e.g., before, during or after sensor insertion into a body). On body electronics may include an in vivo glucose sensor, electronics, battery, and antenna encased (except for the sensor portion that is for in vivo positioning) in a waterproof housing that includes or is attachable to an adhesive pad. In certain embodiments, the housing withstands immersion in about one meter of water for up to at least 30 minutes. In certain embodiments, the housing withstands continuous underwater contact, e.g., for longer than about 30 minutes, and continues to function properly according to its intended use, e.g., without water damage to the housing electronics where the housing is suitable for water submersion.

Embodiments include sensor insertion devices, which also may be referred to herein as sensor delivery units, or the like. Insertion devices may retain on body electronics assemblies completely in an interior compartment, i.e., an insertion device may be "pre-loaded" with on body electronics assemblies during the manufacturing process (e.g., on body electronics may be packaged in a sterile interior compartment of an insertion device). In such embodiments, insertion devices may form sensor assembly packages (including sterile packages) for pre-use or new on body electronics assemblies, and insertion devices configured to apply on body electronics assemblies to recipient bodies.

Embodiments include portable handheld display devices, as separate devices and spaced apart from an on body electronics assembly, that collect information from the assemblies and provide sensor derived analyte readings to users. Such devices may also be referred to as meters, readers, monitors, receivers, human interface devices, companions, or the like. Certain embodiments may include an integrated in vitro analyte meter. In certain embodiments, display devices include one or more wired or wireless communications ports such as USB, serial, parallel, or the like, configured to establish communication between a display device and another unit (e.g., on body electronics, power unit to recharge a battery, a PC, etc.). For example, a display device communication port may enable charging a display device battery with a respective charging cable and/or data exchange between a display device and its compatible informatics software.

Compatible informatics software in certain embodiments include, for example, but are not limited to, stand alone or network connection enabled data management software program, resident or running on a display device, personal computer, a server terminal, for example, to perform data analysis, charting, data storage, data archiving and data communication as well as data synchronization. Informatics software in certain embodiments may also include software for executing field upgradable functions to upgrade firmware of a display device and/or on body electronics unit to upgrade the resident software on the display device and/or the on body electronics unit, e.g., with versions of firmware that include additional features and/or include software bugs or errors fixed, etc.

Embodiments may include a haptic feedback feature such as a vibration motor or the like, configured so that corresponding notifications (e.g., a successful on-demand reading received at a display device), may be delivered in the form of haptic feedback.

Embodiments include programming embedded on a computer readable medium, i.e., computer-based application software (may also be referred to herein as informatics software or programming or the like) that processes analyte information obtained from the system and/or user self-reported data. Application software may be installed on a host computer such as a mobile telephone, PC, an Internet-enabled human interface device such as an Internet-enabled phone, personal digital assistant, or the like, by a display device or an on body electronics unit. Informatics programming may transform data acquired and stored on a display device or on body unit for use by a user.

Embodiments of the subject disclosure are described primarily with respect to glucose monitoring devices and systems, and methods of glucose monitoring, for convenience only and such description is in no way intended to limit the scope of the disclosure. It is to be understood that the analyte monitoring system may be configured to monitor a variety of analytes at the same time or at different times.

For example, analytes that may be monitored include, but are not limited to, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times, with a single sensor or with a plurality of sensors which may use the same on body electronics (e.g., simultaneously) or with different on body electronics.

As described in detail below, embodiments include devices, systems, kits and/or methods to monitor one or more physiological parameters such as, for example, but not limited to, analyte levels, temperature levels, heart rate, user activity level, over a predetermined monitoring time period. Also provided are methods of manufacturing. Predetermined monitoring time periods may be less than about 1 hour, or may include about 1 hour or more, e.g., about a few hours or more, e.g., about a few days of more, e.g., about 3 or more days, e.g., about 5 days or more, e.g., about 7 days or more, e.g., about 10 days or more, e.g., about 14 days or more, e.g., about several weeks, e.g., about 1 month or more. In certain embodiments, after the expiration of the predetermined monitoring time period, one or more features of the system may be automatically deactivated or disabled at the on body electronics assembly and/or display device.

For example, a predetermined monitoring time period may begin with positioning the sensor in vivo and in contact with a body fluid such as ISF, and/or with the initiation (or powering on to full operational mode) of the on body electronics. Initialization of on body electronics may be implemented with a command generated and transmitted by a display device in response to the activation of a switch and/or by placing the display device within a predetermined distance (e.g., close proximity) to the on body electronics, or by user manual activation of a switch on the on body electronics unit, e.g., depressing a button, or such activation may be caused by the insertion device, e.g., as described in U.S. patent application Ser. No. 12/698,129, now U.S. Pat. No. 9,402,544, and U.S. Provisional Application Nos. 61/238,646, 61/246,825, 61/247,516, 61/249,535, 61/317, 243, 61/345,562, and 61/361,374, the disclosures of each of which are incorporated herein by reference for all purposes.

When initialized in response to a received command from a display device, the on body electronics retrieves and executes from its memory software routine to fully power on the components of the on body electronics, effectively placing the on body electronics in full operational mode in response to receiving the activation command from the display device. For example, prior to the receipt of the command from the display device, a portion of the components in the on body electronics may be powered by its internal power supply such as a battery while another portion of the components in the on body electronics may be in powered down or low power including no power, inactive mode, or all components may be in an inactive mode, powered down mode. Upon receipt of the command, the remaining portion (or all) of the components of the on body electronics is switched to active, fully operational mode.

Embodiments of on body electronics may include one or more circuit boards with electronics including control logic implemented in ASIC, microprocessors, memory, and the like, and transcutaneously positionable analyte sensors forming a single assembly. On body electronics may be configured to provide one or more signals or data packets associated with a monitored analyte level upon detection of a display device of the analyte monitoring system within a predetermined proximity for a period of time (for example, about 2 minutes, e.g., 1 minute or less, e.g., about 30 seconds or less, e.g., about 10 seconds or less, e.g., about 5 seconds or less, e.g., about 2 seconds or less) and/or until a confirmation, such as an audible and/or visual and/or tactile (e.g., vibratory) notification, is output on the display device indicating successful acquisition of the analyte related signal from the on body electronics. A distinguishing notification may also be output for unsuccessful acquisition in certain embodiments.

In certain embodiments, the monitored analyte level may be correlated and/or converted to glucose levels in blood or other fluids such as ISF. Such conversion may be accomplished with the on body electronics, but in many embodiments will be accomplished with display device electronics. In certain embodiments, glucose level is derived from the monitored analyte level in the ISF.

Analyte sensors may be insertable into a vein, artery, or other portion of the body containing analyte. In certain embodiments, analyte sensors may be positioned in contact with ISF to detect the level of analyte, where the detected analyte level may be used to infer the user's glucose level in blood or interstitial tissue.

Embodiments include transcutaneous sensors and also wholly implantable sensors and wholly implantable assemblies in which a single assembly including the analyte sensor and electronics are provided in a sealed housing (e.g., hermetically sealed biocompatible housing) for implantation in a user's body for monitoring one or more physiological parameters.

Embodiments of In Vivo Analyte Monitoring Systems

Figure 1B:
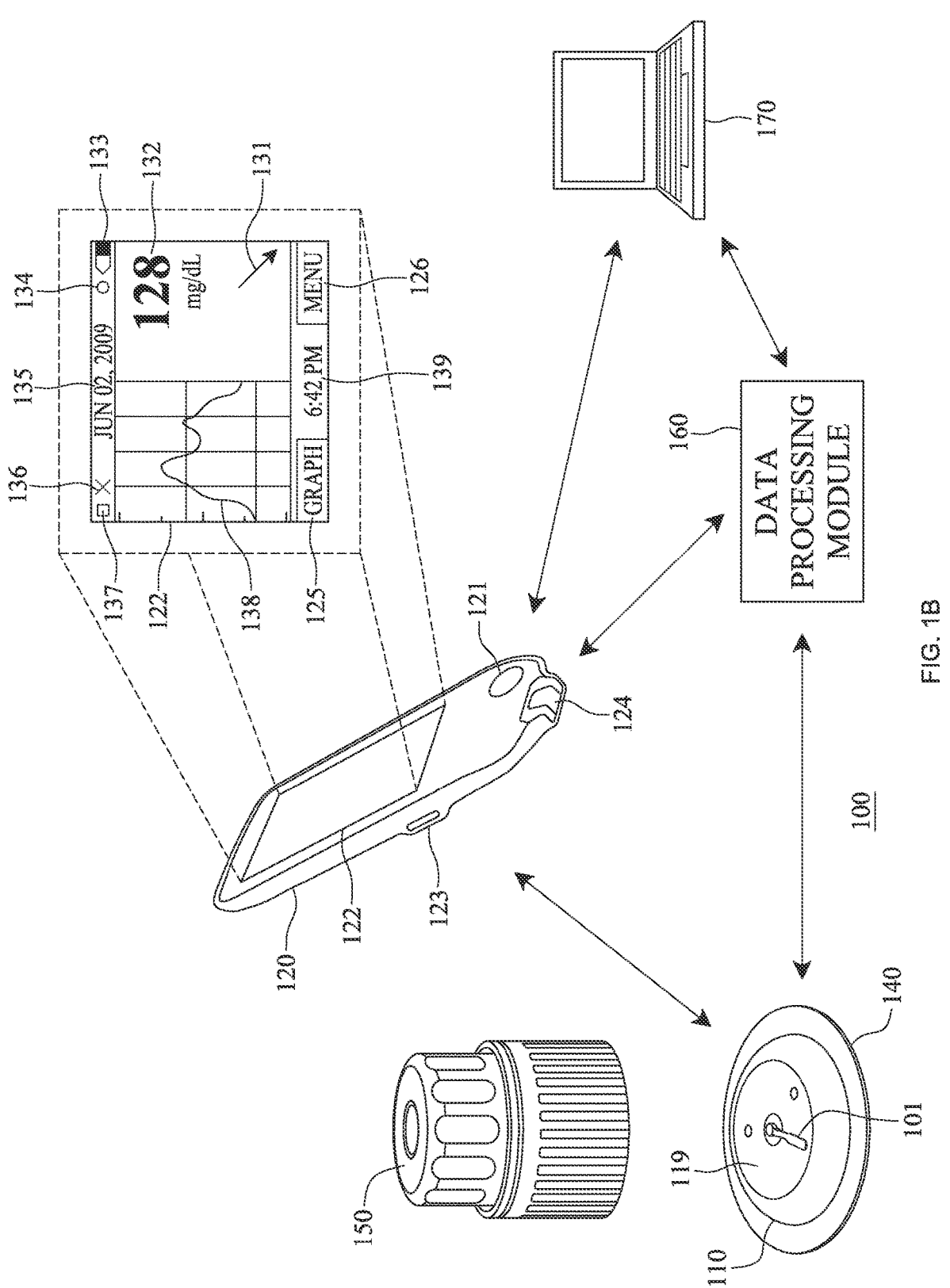
FIG. 1B illustrates a schematic diagram of the elements of FIG. 1A.

FIGS. 1A and 1B show an exemplary in vivo-based analyte monitoring system 100 in accordance with embodiments of the present disclosure. As shown, in certain embodiments, analyte monitoring system 100 includes on body electronics 110 electrically coupled to in vivo analyte sensor 101 and attached to adhesive layer 140 for attachment on a skin surface on the body of a user. On body electronics 110 includes on body housing 119, that defines an interior compartment. Also shown in FIG. 1B is insertion device 150 that, when operated, transcutaneously positions a portion of analyte sensor 101 through a skin surface and in fluid contact with interstitial fluid, and positions on body electronics 110 and adhesive layer 140 on a skin surface. In certain embodiments, on body electronics 110, analyte sensor 101 and adhesive layer 140 are sealed within the housing of insertion device 150 before use, and in certain embodiments, adhesive layer 140 is also sealed within the housing or itself provides a terminal seal of the insertion device 150. Devices, systems and methods that may be used with embodiments herein are described, e.g., in U.S. patent application Ser. No. 12/698, 129, now U.S. Pat. No. 9,402,544, and U.S. Provisional Application Nos. 61/238,646, 61/246,825, 61/247,516, 61/249,535, 61/317,243, 61/345,562, and 61/361,374, the disclosures of each of which are incorporated herein by reference for all purposes.

Referring back to the FIG. 1B, analyte monitoring system 100 includes display device 120 which includes a display 122 to output information to the user, an input component 121 such as a button, actuator, a touch sensitive switch, a capacitive switch, pressure sensitive switch, jog wheel or the like, to input data or command to display device 120 or otherwise control the operation of display device 120. It is noted that some embodiments may include display-less devices or devices without any user interface components. These devices may be functionalized to store data as a data logger and/or provide a conduit to transfer data from on body electronics and/or a display-less device to another device and/or location. Embodiments will be described herein as display devices for exemplary purposes which are in no way intended to limit the embodiments of the present disclosure. It will be apparent that display-less devices may also be used in certain embodiments.

In certain embodiments, on body electronics 110 may be configured to store some or all of the monitored analyte related data received from analyte sensor 101 in a memory during the monitoring time period, and maintain it in memory until the usage period ends. In such embodiments, stored data is retrieved from on body electronics 110 at the conclusion of the monitoring time period, for example, after removing analyte sensor 101 from the user by detaching on body electronics 110 from the skin surface where it was positioned during the monitoring time period. In such data logging configurations, real time monitored analyte level is not communicated to display device 120 during the monitoring period or otherwise transmitted from on body electronics 110, but rather, retrieved from on body electronics 110 after the monitoring time period.

In certain embodiments, input component 121 of display device 120 may include a microphone and display device 120 may include software configured to analyze audio input received from the microphone, such that functions and operation of the display device 120 may be controlled by voice commands. In certain embodiments, an output component of display device 120 includes a speaker for outputting information as audible signals. Similar voice responsive components such as a speaker, microphone and software routines to generate, process and store voice driven signals may be provided to on body electronics 110.

In certain embodiments, display 122 and input component 121 may be integrated into a single component, for example a display that can detect the presence and location of a physical contact touch upon the display such as a touch screen user interface. In such embodiments, the user may control the operation of display device 120 by utilizing a set of pre-programmed motion commands, including, but not limited to, single or double tapping the display, dragging a finger or instrument across the display, motioning multiple fingers or instruments toward one another, motioning multiple fingers or instruments away from one another, etc. In certain embodiments, a display includes a touch screen having areas of pixels with single or dual function capacitive elements that serve as LCD elements and touch sensors.

Display device 120 also includes data communication port 123 for wired data communication with external devices such as remote terminal (personal computer) 170, for example. Example embodiments of the data communication port 123 include USB port, mini USB port, RS-232 port, Ethernet port, Firewire port, or other similar data communication ports configured to connect to the compatible data cables. Display device 120 may also include an integrated in vitro glucose meter, including in vitro test strip port 124 to receive an in vitro glucose test strip for performing in vitro blood glucose measurements.

Referring still to FIG. 1B, display 122 in certain embodiments is configured to display a variety of information—some or all of which may be displayed at the same or different time on display 122. In certain embodiments the displayed information is user-selectable so that a user can customize the information shown on a given display screen. Display 122 may include but is not limited to graphical display 138, for example, providing a graphical output of glucose values over a monitored time period (which may show important markers such as meals, exercise, sleep, heart rate, blood pressure, etc., numerical display 132, for example, providing monitored glucose values (acquired or received in response to the request for the information), and trend or directional arrow display 131 that indicates a rate of analyte change and/or a rate of the rate of analyte change, e.g., by moving locations on display 122.

As further shown in FIG. 1B, display 122 may also include date display 135 providing for example, date information for the user, time of day information display 139 providing time of day information to the user, battery level indicator display 133 which graphically shows the condition of the battery (rechargeable or disposable) of the display device 120, sensor calibration status icon display 134 for example, in monitoring systems that require periodic, routine or a predetermined number of user calibration events, notifying the user that the analyte sensor calibration is necessary, audio/vibratory settings icon display 136 for displaying the status of the audio/vibratory output or alarm state, and wireless connectivity status icon display 137 that provides indication of wireless communication connection with other devices such as on body electronics, data processing module 160, and/or remote terminal 170. As additionally shown in FIG. 1B, display 122 may further include simulated touch screen button 125, 126 for accessing menus, changing display graph output configurations or otherwise for controlling the operation of display device 120.

Referring back to FIG. 1B, in certain embodiments, display 122 of display device 120 may be additionally, or instead of visual display, configured to output alarms notifications such as alarm and/or alert notifications, glucose values etc., which may be audible, tactile, or any combination thereof. In one aspect, the display device 120 may include other output components such as a speaker, vibratory output component and the like to provide audible and/or vibratory output indication to the user in addition to the visual output indication provided on display 122. Further details and other display embodiments can be found in, e.g., U.S. patent application Ser. No. 12/871,901, now U.S. Pat. No. 8,514,086, U.S. Provisional Application Nos. 61/238, 672, 61/247,541, 61/297,625, the disclosures of each of which are incorporated herein by reference for all purposes.

After the positioning of on body electronics 110 on the skin surface and analyte sensor 101 in vivo to establish fluid contact with interstitial fluid (or other appropriate body fluid), on body electronics 110 in certain embodiments is configured to wirelessly communicate analyte related data (such as, for example, data corresponding to monitored analyte level and/or monitored temperature data, and/or stored historical analyte related data) when on body electronics 110 receives a command or request signal from display device 120. In certain embodiments, on body electronics 110 may be configured to at least periodically broadcast real time data associated with monitored analyte level which is received by display device 120 when display device 120 is within communication range of the data broadcast from on body electronics 110, i.e., it does not need a command or request from a display device to send information.

For example, display device 120 may be configured to transmit one or more commands to on body electronics 110 to initiate data transfer, and in response, on body electronics 110 may be configured to wirelessly transmit stored analyte related data collected during the monitoring time period to display device 120. Display device 120 may in turn be connected to a remote terminal 170 such as a personal computer and functions as a data conduit to transfer the stored analyte level information from the on body electronics 110 to remote terminal 170. In certain embodiments, the received data from the on body electronics 110 may be stored (permanently or temporarily) in one or more memory of the display device 120. In certain other embodiments, display device 120 is configured as a data conduit to pass the data received from on body electronics 110 to remote terminal 170 that is connected to display device 120.

Referring still to FIG. 1B, also shown in analyte monitoring system 100 are data processing module 160 and remote terminal 170. Remote terminal 170 may include a personal computer, a server terminal a laptop computer or other suitable data processing devices including software for data management and analysis and communication with the components in the analyte monitoring system 100. For example, remote terminal 170 may be connected to a local area network (LAN), a wide area network (WAN), or other data network for uni-directional or bi-directional data communication between remote terminal 170 and display device 120 and/or data processing module 160.

Remote terminal 170 in certain embodiments may include one or more computer terminals located at a physician's office or a hospital. For example, remote terminal 170 may be located at a location other than the location of display device 120. Remote terminal 170 and display device 120 could be in different rooms or different buildings. Remote terminal 170 and display device 120 could be at least about one mile apart, e.g., at least about 10 miles apart, e.g., at least about 100 miles apart. For example, remote terminal 170 could be in the same city as display device 120, remote terminal 170 could be in a different city than display device 120, remote terminal 170 could be in the same state as display device 120, remote terminal 170 could be in a different state than display device 120, remote terminal 170 could be in the same country as display device 120, or remote terminal 170 could be in a different country than display device 120, for example.

In certain embodiments, a separate, optional data communication/processing device such as data processing module 160 may be provided in analyte monitoring system 100. Data processing module 160 may include components to communicate using one or more wireless communication protocols such as, for example, but not limited to, infrared (IR) protocol, Bluetooth® protocol, Zigbee® protocol, and 802.11 wireless LAN protocol. Additional description of communication protocols including those based on Bluetooth® protocol and/or Zigbee® protocol can be found in U.S. Patent Publication No. 2006/0193375 incorporated herein by reference for all purposes. Data processing module 160 may further include communication ports, drivers or connectors to establish wired communication with one or more of display device 120, on body electronics 110, or remote terminal 170 including, for example, but not limited to USB connector and/or USB port, Ethernet connector and/or port, FireWire connector and/or port, or RS-232 port and/or connector.

In certain embodiments, data processing module 160 is programmed to transmit a polling or query signal to on body electronics 110 at a predetermined time interval (e.g., once every minute, once every five minutes, or the like), and in response, receive the monitored analyte level information from on body electronics 110. Data processing module 160 stores in its memory the received analyte level information, and/or relays or retransmits the received information to another device such as display device 120. More specifically in certain embodiments, data processing module 160 may be configured as a data relay device to retransmit or pass through the received analyte level data from on body electronics 110 to display device 120 or a remote terminal (for example, over a data network such as a cellular or WiFi data network) or both.

In certain embodiments, on body electronics 110 and data processing module 160 may be positioned on the skin surface of the user within a predetermined distance of each other (for example, about 1-12 inches, or about 1-10 inches, or about 1-7 inches, or about 1-5 inches) such that periodic communication between on body electronics 110 and data processing module 160 is maintained. Alternatively, data processing module 160 may be worn on a belt or clothing item of the user, such that the desired distance for communication between the on body electronics 110 and data processing module 160 for data communication is maintained. In a further aspect, the housing of data processing module 160 may be configured to couple to or engage with on body electronics 110 such that the two devices are combined or integrated as a single assembly and positioned on the skin surface. In further embodiments, data processing module 160 is detachably engaged or connected to on body electronics 110 providing additional modularity such that data processing module 160 may be optionally removed or reattached as desired.

Referring again to FIG. 1B, in certain embodiments, data processing module 160 is programmed to transmit a command or signal to on body electronics 110 at a predetermined time interval such as once every minute, or once every 5 minutes or once every 30 minutes or any other suitable or desired programmable time interval to request analyte related data from on body electronics 110. When data processing module 160 receives the requested analyte related data, it stores the received data. In this manner, analyte monitoring system 100 may be configured to receive the continuously monitored analyte related information at the programmed or programmable time interval, which is stored and/or displayed to the user. The stored data in data processing module 160 may be subsequently provided or transmitted to display device 120, remote terminal 170 or the like for subsequent data analysis such as identifying frequency of periods of glycemic level excursions over the monitored time period, or the frequency of the alarm event occurrence during the monitored time period, for example, to improve therapy related decisions. Using this information, the doctor, healthcare provider or the user may adjust or recommend modification to the diet, daily habits and routines such as exercise, and the like.

In another embodiment, data processing module 160 transmits a command or signal to on body electronics 110 to receive the analyte related data in response to a user activation of a switch provided on data processing module 160 or a user initiated command received from display device 120. In further embodiments, data processing module 160 is configured to transmit a command or signal to on body electronics 110 in response to receiving a user initiated command only after a predetermined time interval has elapsed. For example, in certain embodiments, if the user does not initiate communication within a programmed time period, such as, for example about 5 hours from last communication (or 10 hours from the last communication, or 24 hours from the last communication), the data processing module 160 may be programmed to automatically transmit a request command or signal to on body electronics 110. Alternatively, data processing module 160 may be programmed to activate an alarm to notify the user that a predetermined time period of time has elapsed since the last communication between the data processing module 160 and on body electronics 110. In this manner, users or healthcare providers may program or configure data processing module 160 to provide certain compliance with analyte monitoring regimen, so that frequent determination of analyte levels is maintained or performed by the user.

In certain embodiments, when a programmed or programmable alarm condition is detected (for example, a detected glucose level monitored by analyte sensor 101 that is outside a predetermined acceptable range indicating a physiological condition which requires attention or intervention for medical treatment or analysis (for example, a hypoglycemic condition, a hyperglycemic condition, an impending hyperglycemic condition or an impending hypoglycemic condition), the one or more output indications may be generated by the control logic or processor of the on body electronics 110 and output to the user on a user interface of on body electronics 110 so that corrective action may be timely taken. In addition to or alternatively, if display device 120 is within communication range, the output indications or alarm data may be communicated to display device 120 whose processor, upon detection of the alarm data reception, controls the display 122 to output one or more notification.

In certain embodiments, control logic or microprocessors of on body electronics 110 include software programs to determine future or anticipated analyte levels based on information obtained from analyte sensor 101, e.g., the current analyte level, the rate of change of the analyte level, the acceleration of the analyte level change, and/or analyte trend information determined based on stored monitored analyte data providing a historical trend or direction of analyte level fluctuation as function time during monitored time period. Predictive alarm parameters may be programmed or programmable in display device 120, or the on body electronics 110, or both, and output to the user in advance of anticipating the user's analyte level reaching the future level. This provides the user an opportunity to take timely corrective action.

Information, such as variation or fluctuation of the monitored analyte level as a function of time over the monitored time period providing analyte trend information, for example, may be determined by one or more control logic or microprocessors of display device 120, data processing module 160, and/or remote terminal 170, and/or on body electronics 110. Such information may be displayed as, for example, a graph (such as a line graph) to indicate to the user the current and/or historical and/or and predicted future analyte levels as measured and predicted by the analyte monitoring system 100. Such information may also be displayed as directional arrows (for example, see trend or directional arrow display 131) or other icon(s), e.g., the position of which on the screen relative to a reference point indicated whether the analyte level is increasing or decreasing as well as the acceleration or deceleration of the increase or decrease in analyte level. This information may be utilized by the user to determine any necessary corrective actions to ensure the analyte level remains within an acceptable and/or clinically safe range. Other visual indicators, including colors, flashing, fading, etc., as well as audio indicators including a change in pitch, volume, or tone of an audio output and/or vibratory or other tactile indicators may also be incorporated into the display of trend data as means of notifying the user of the current level and/or direction and/or rate of change of the monitored analyte level. For example, based on a determined rate of glucose change, programmed clinically significant glucose threshold levels (e.g., hyperglycemic and/or hypoglycemic levels), and current analyte level derived by an in vivo analyte sensor, the system 100 may include an algorithm stored on computer readable medium to determine the time it will take to reach a clinically significant level and will output notification in advance of reaching the clinically significant level, e.g., 30 minutes before a clinically significant level is anticipated, and/or 20 minutes, and/or 10 minutes, and/or 5 minutes, and/or 3 minutes, and/or 1 minute, and so on, with outputs increasing in intensity or the like.

Referring again back to FIG. 1B, in certain embodiments, software algorithm(s) for execution by data processing module 160 may be stored in an external memory device such as an SD card, microSD card, compact flash card, XD card, Memory Stick card, Memory Stick Duo card, or USB memory stick/device including executable programs stored in such devices for execution upon connection to the respective one or more of the on body electronics 110, remote terminal 170 or display device 120. In a further aspect, software algorithms for execution by data processing module 160 may be provided to a communication device such as a mobile telephone including, for example, WiFi or Internet enabled smart phones or personal digital assistants (PDAs) as a downloadable application for execution by the downloading communication device.

Examples of smart phones include Windows®, Android®, iPhone® operating system, Palm® WebOS®, Blackberry® operating system, or Symbian® operating system based mobile telephones with data network connectivity functionality for data communication over an internet connection and/or a local area network (LAN). PDAs as described above include, for example, portable electronic devices including one or more microprocessors and data communication capability with a user interface (e.g., display/output unit and/or input unit, and configured for performing data processing, data upload/download over the internet, for example. In such embodiments, remote terminal 170 may be configured to provide the executable application software to the one or more of the communication devices described above when communication between the remote terminal 170 and the devices are established.

In still further embodiments, executable software applications may be provided over-the-air (OTA) as an OTA download such that wired connection to remote terminal 170 is not necessary. For example, executable applications may be automatically downloaded as software download to the communication device, and depending upon the configuration of the communication device, installed on the device for use automatically, or based on user confirmation or acknowledgement on the communication device to execute the installation of the application. The OTA download and installation of software may include software applications and/or routines that are updates or upgrades to the existing functions or features of data processing module 160 and/or display device 120.

Referring back to remote terminal 170 of FIG. 1B, in certain embodiments, new software and/or software updates such as software patches or fixes, firmware updates or software driver upgrades, among others, for display device 120 and/or on body electronics 110 and/or data processing module 160 may be provided by remote terminal 170 when communication between the remote terminal 170 and display device 120 and/or data processing module 160 is established. For example, software upgrades, executable programming changes or modification for on body electronics 110 may be received from remote terminal 170 by one or more of display device 120 or data processing module 160, and thereafter, provided to on body electronics 110 to update its software or programmable functions. For example, in certain embodiments, software received and installed in on body electronics 110 may include software bug fixes, modification to the previously stalled software parameters (modification to analyte related data storage time interval, resetting or adjusting time base or information of on body electronics 110, modification to the transmitted data type, data transmission sequence, or data storage time period, among others). Additional details describing field upgradability of software of portable electronic devices, and data processing are provided in U.S. patent application Ser. Nos. 12/698,124, 12/794,721, now U.S. Pat. No. 8,595,607, Ser. Nos. 12/699,653, and 12/699,844, and U.S. Provisional Application Nos. 61/359,265, and 61/325,155, the disclosures of which are incorporated by reference herein for all purposes.

Referring to FIGS. 1A and 1B, an analyte monitoring system 100 can generally include, in accordance with one embodiment, an on-body analyte monitoring device, a receiver 120, data processing terminal 170, and secondary receiver unit 106. Generally, analyte sensor 101 operatively contacts an analyte to be monitored in a biological fluid, such as, but not limited to, blood or interstitial fluid, and converts the contacted analyte level into data signals relating to the amount or concentration of the analyte. The data signals are communicated to the on body electronics 110, which is in electrical communication with analyte sensor 101. The electronics unit can be a separate and distinct component, or can be integrated with the analyte sensor to define a single component. The on body electronics 110 processes the data signals (e.g., encodes signals) received from analyte sensor 101 and transmits the processed data signals to receiver 120, e.g., a primary receiver, along a communication link 103. The communication between on body electronics 110 and receiver 120 can be either unidirectional or bidirectional.

Figure 2:
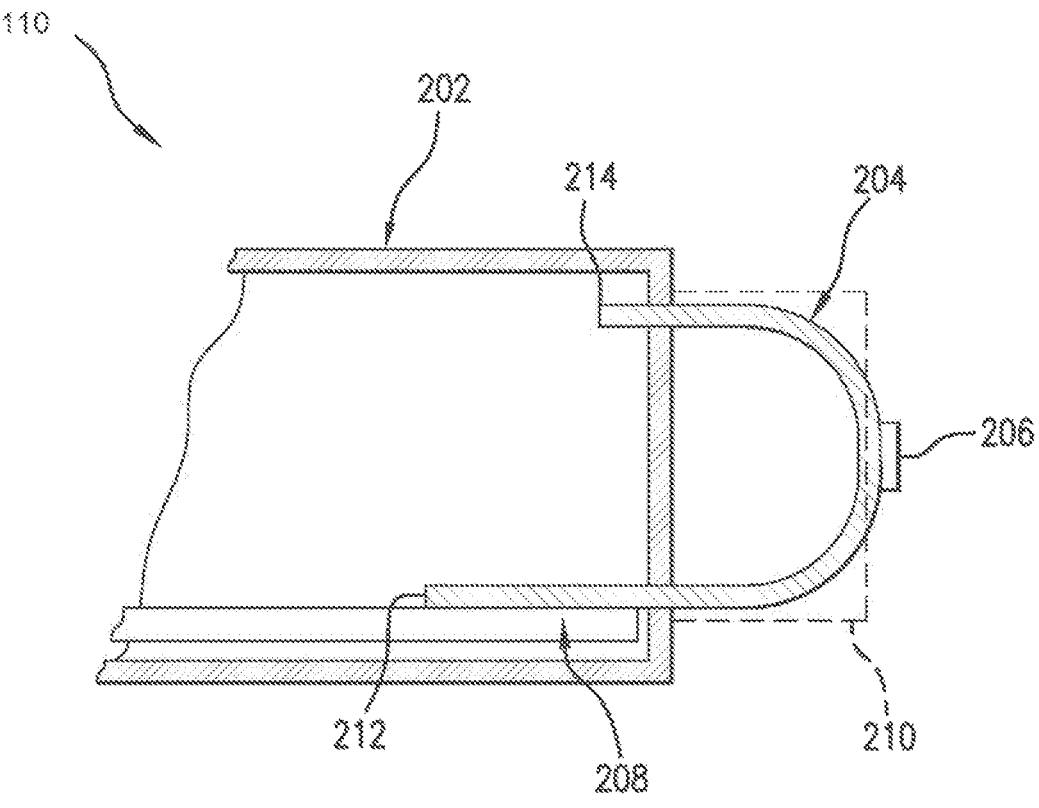
FIG. 2 illustrates a schematic view of an electronics unit according to one or more embodiments of the present invention.

In one aspect of the invention, an interconnect is provided to establish electrical communication with a transmitter, transceiver, communications circuit or other electronics. For example, as illustrated in FIG. 2, on-body electronics unit 110 comprises a body including housing 202. The housing includes a top wall connected to a bottom wall by a sidewall. An elongate interconnect 204 can be coupled to the on body electronics 110. The elongate interconnect 204 comprises conductive material disposed at least partially along a body having a first end 212 coupled, e.g., permanently affixed or removably fixed, to housing 202. In one embodiment, the first end 212 can be secured to a printed circuit board 208 disposed in the body of the on body electronics 110. The elongate interconnect can further include a second end 214 engaged to the on body electronics body, for example, the second end 214 in some embodiments, can be engaged to the housing 202, such as slidingly engaged, for example at an end opposite the first end 212. Alternatively, the second end of interconnect 204 may be permanently affixed to the opposite side of housing 202.

As shown in FIG. 2, a length of the elongate interconnect body 204 can be configured to extend laterally from a sidewall of the housing 202. In one embodiment, the elongate interconnect 204 body can include a generally U-shaped configuration along its length. As such, the interconnect can be configured to physically contact an analyte sensor disposed proximate the on body electronics body.

In some embodiments, a conductive contact 206 can be located along a length of the elongate interconnect 204. The contact plate is configured to contact an analyte sensor and establish electrical conductivity between the on body electronics and the analyte sensor. (See FIG. 4). As described, the elongate interconnect comprises conductive material. In one embodiment, the conductive material defines one or more conductive areas along the body of the interconnect. The conductive areas can include one or more conductive contacts and one or more conductive traces disposed between conductive contacts along at least a portion of the length of the elongate interconnect body. Thus, when in direct contact with the electronic circuitry of the on body electronics and/or a sensor, electrical communications can be established.

Figure 3:
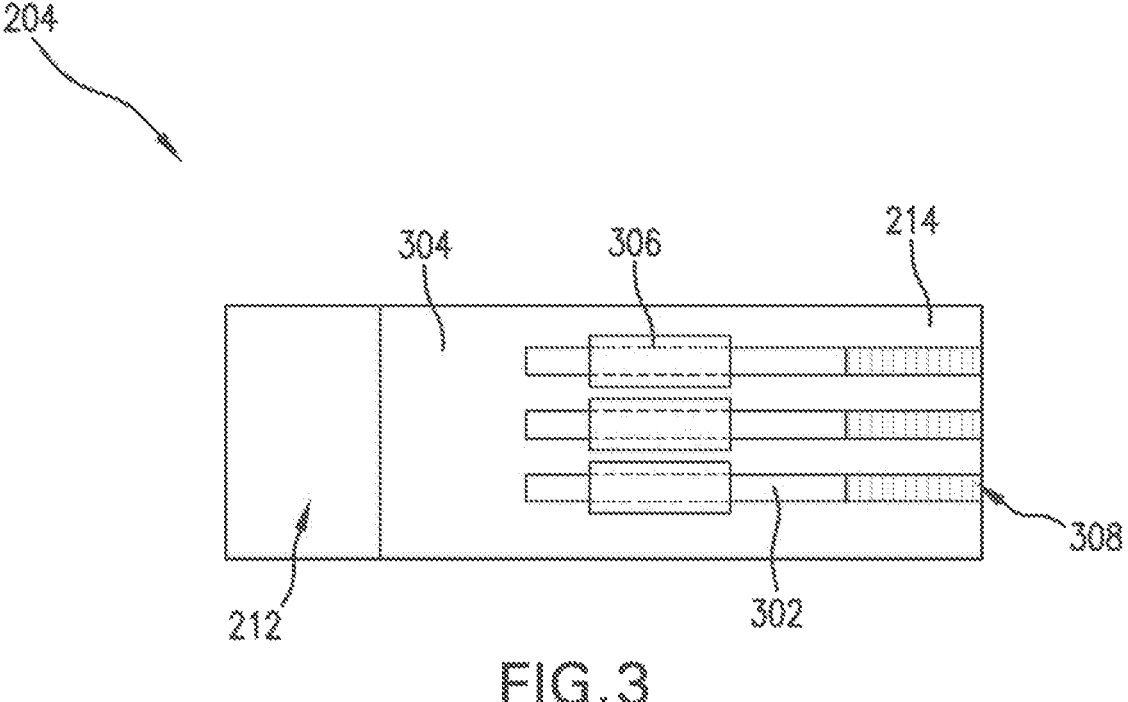
FIG. 3 illustrates a schematic view of the elongate interconnect of the electronics unit of FIG. 2 in a flat position.

For example, referring now to FIG. 3, one embodiment of elongate interconnect 204 includes the one or more conductive areas defined by conductive material 302, 306, 308. As shown, conductive traces 302 extend between conductive contacts 306 and 308. In this manner, the elongate interconnect includes a conductive surface attachable to the on body electronics, which can establish electrical communication with the on body electronics during contact.

In some embodiments, the conductive material of elongate interconnect includes conductive traces 302 embedded in a flexible material, such as a flexible strip 304, which generally can be formed from a thermoplastic material. Suitable thermoplastic materials include polyimides such as Apical, Kapton, UPILEX, VTEC PI, Norton TH and Kaptrex. In other embodiments, conductive traces 302 are encapsulated in a flexible sheath. The elongate interconnect can further include conductive films and tapes as described infra.

Suitable elongate interconnects 204 include those depicted in FIGS. 5A-5D. As illustrated, the elongate interconnect can comprise conductive material including conductive cables, including but not limited to high speed ribbon cables, microquick twist ribbon cables, microZip cables, mini probe cables, quick twist cables, ribbonized automation cables, shielded flat ribbon cables, or wide pitch ribbon cables, as illustrated in FIGS. 5A to 5D. In addition, other suitable elongate interconnects include All Flex®, Molex®, Tech-Etch®, and Teknoflex®.

The conductive material associated with the interconnect, as well as the on body electronics and/or analyte sensor, can comprise a non-corroding metal or carbon wire. Suitable conductive materials include, for example, vitreous carbon, graphite, silver, silver-chloride, platinum, palladium, or gold. The conductive material disposed on the component part, e.g., interconnect, sensor, or on body electronics, can comprise a combination of conductive metals, alloys and polymers. In this regard, for example, the electrodes and the conductive traces and/or conductive contacts can be formed from different conductive materials. The conductive material can be applied to the substrate by various techniques including laser ablation, printing, etching, and photolithography. However, any suitable conductive material may be utilized.

Referring back to FIG. 3, conductive contact 306, which is located proximate first end 212, can establish electrical communication with the on body electronics 110, for example, the printed circuit board. The electrical communication in the form of electrical signals can travel towards or from the analyte sensor (not shown) via the conductive traces 302 and conductive contacts 308. Similarly, conductive area 308, located along a length of elongate member 204, allows conductive traces 302 to be in electrical communication with conductive contact 206 (not shown) such that a closed circuit is established between the analyte sensor, interconnect and on body electronics.

In one embodiment, on body electronics 110 includes a temperature sensor. For each sampled signal from analyte sensor 101, the temperature sensor can provide measured temperature information. In another embodiment, on body electronics 110 includes a low-temperature monitor that disables communication from on body electronics 110 if the measured temperature falls below a predefined threshold (e.g., below 5° C.). This is done to protect the on body electronics from over-stressing the energy source of the on body electronics under low-temperature conditions. If the temperature rises above the predefined threshold, the low-temperature monitor enables communication from on body electronics 110.

In accordance with another aspect of the invention, on body electronics 110 includes a low battery voltage monitor that disables the energy source of the on body electronics if the voltage level is too low to reliably transmit communication. The temperature sensor, low-temperature monitor, and the low battery voltage monitor may be controlled via a processor located in on body electronics 110. In a preferred embodiment, the processor is an application specific integrated circuit (ASIC).

Figure 4:
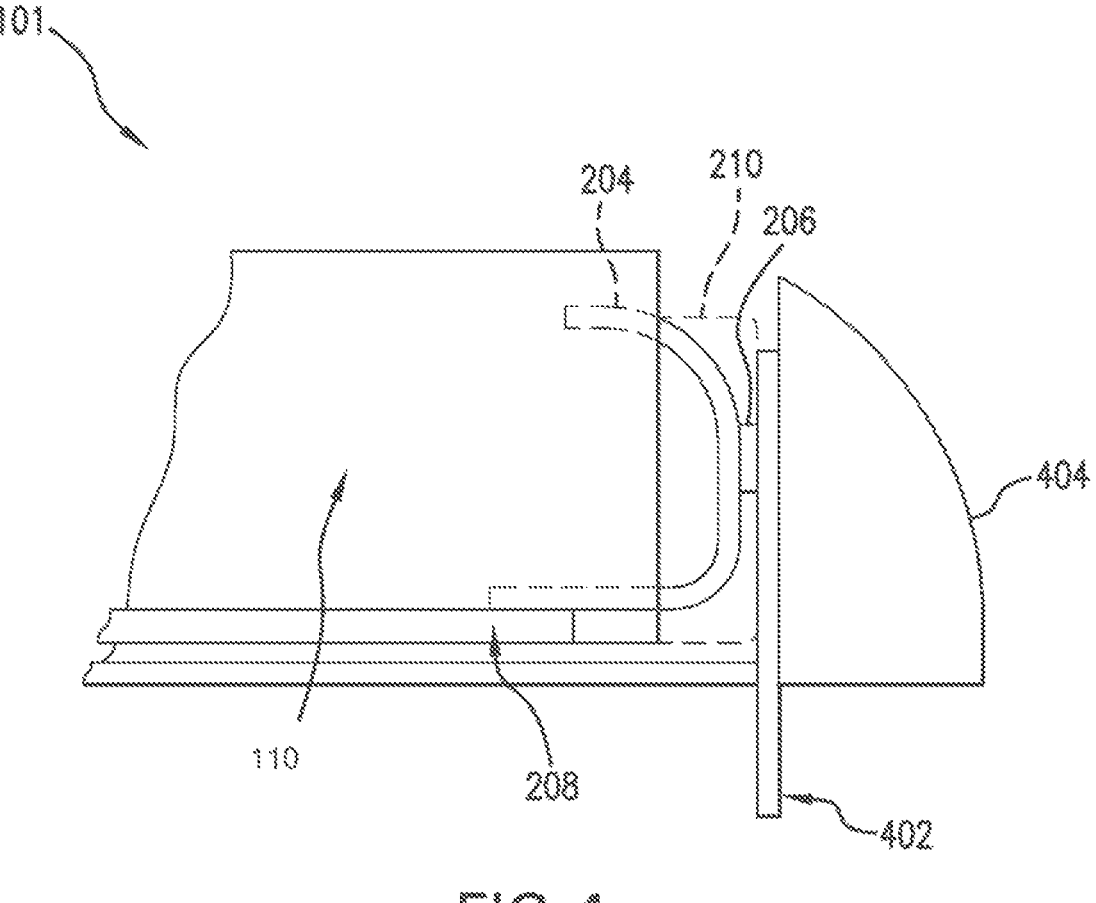
FIG. 4 illustrates a schematic view of the electronics unit of FIG. 2 when it is in contact with an analyte sensor.
Figure 5A:
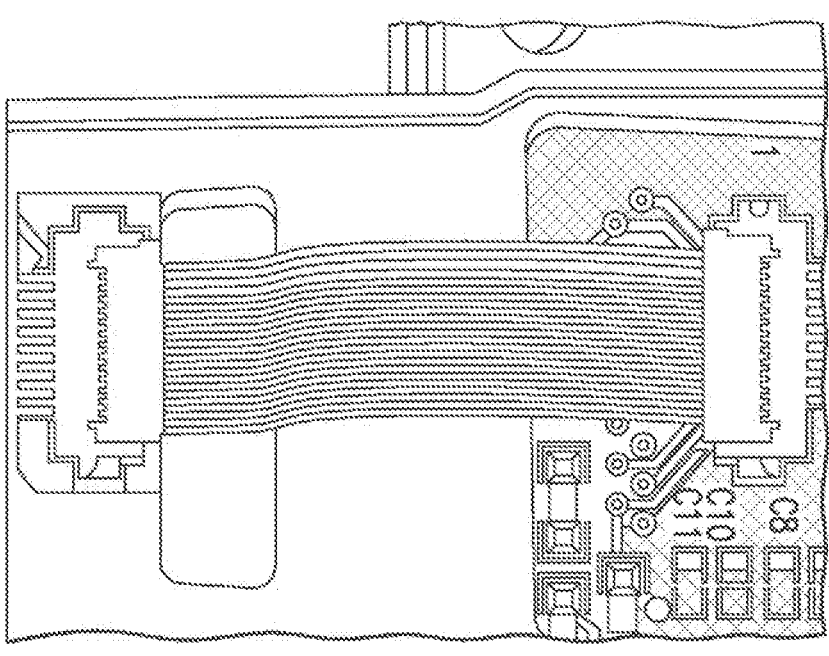
FIGS. 5A-5D depict various elongate interconnects compatible with one or more embodiments of the present invention.
Figure 5B:
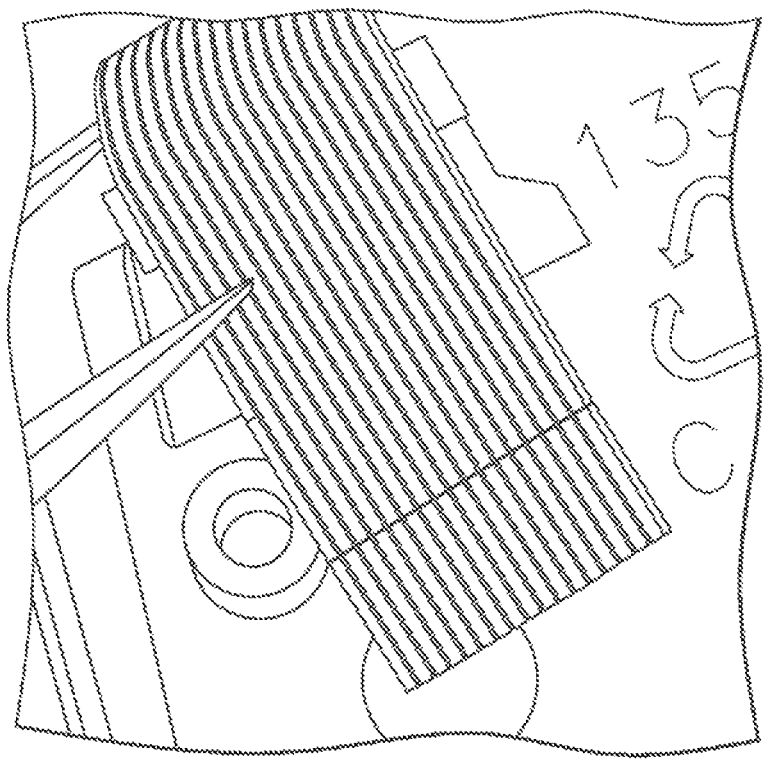
Figure 5C:
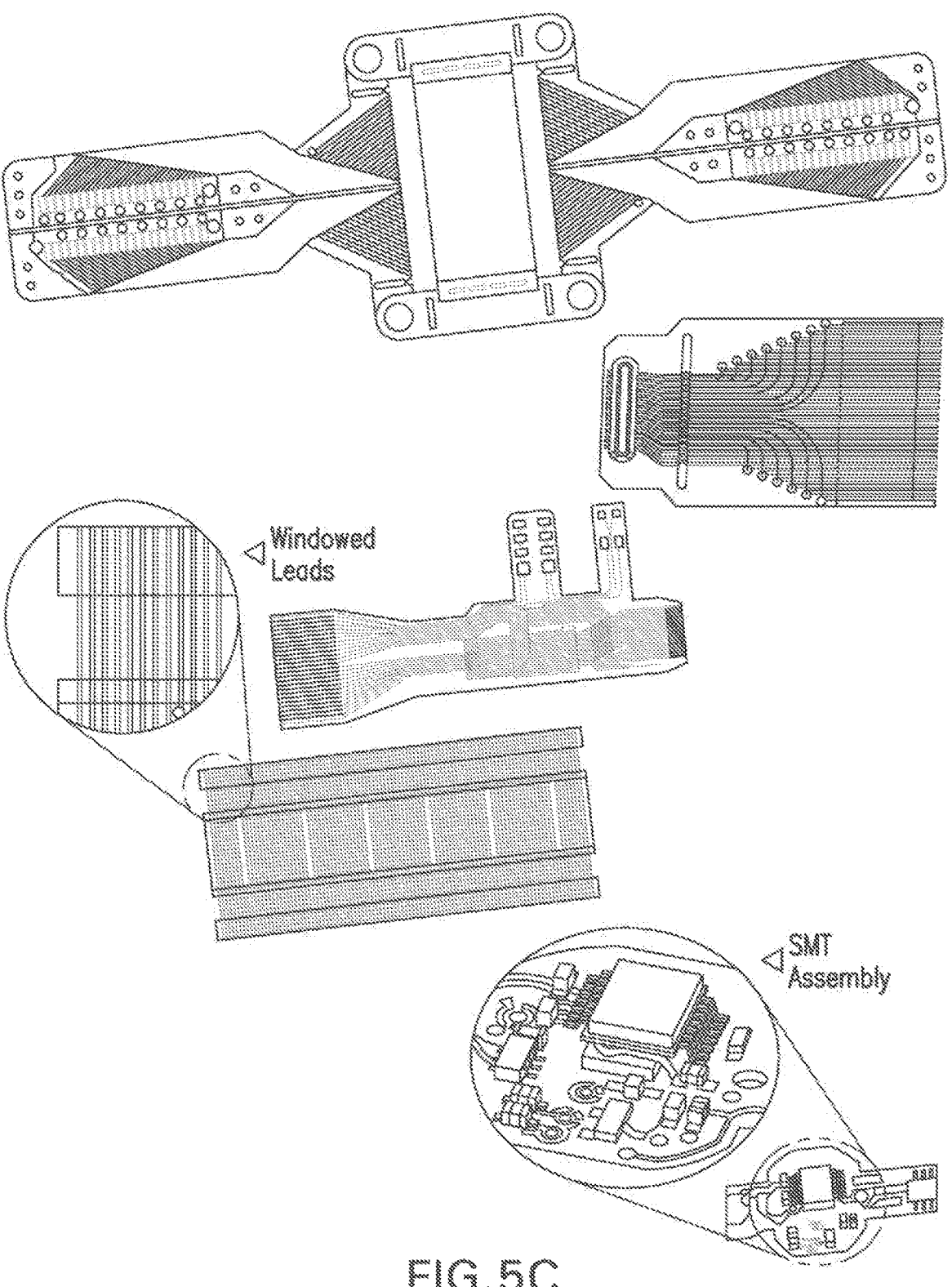
Figure 5D:
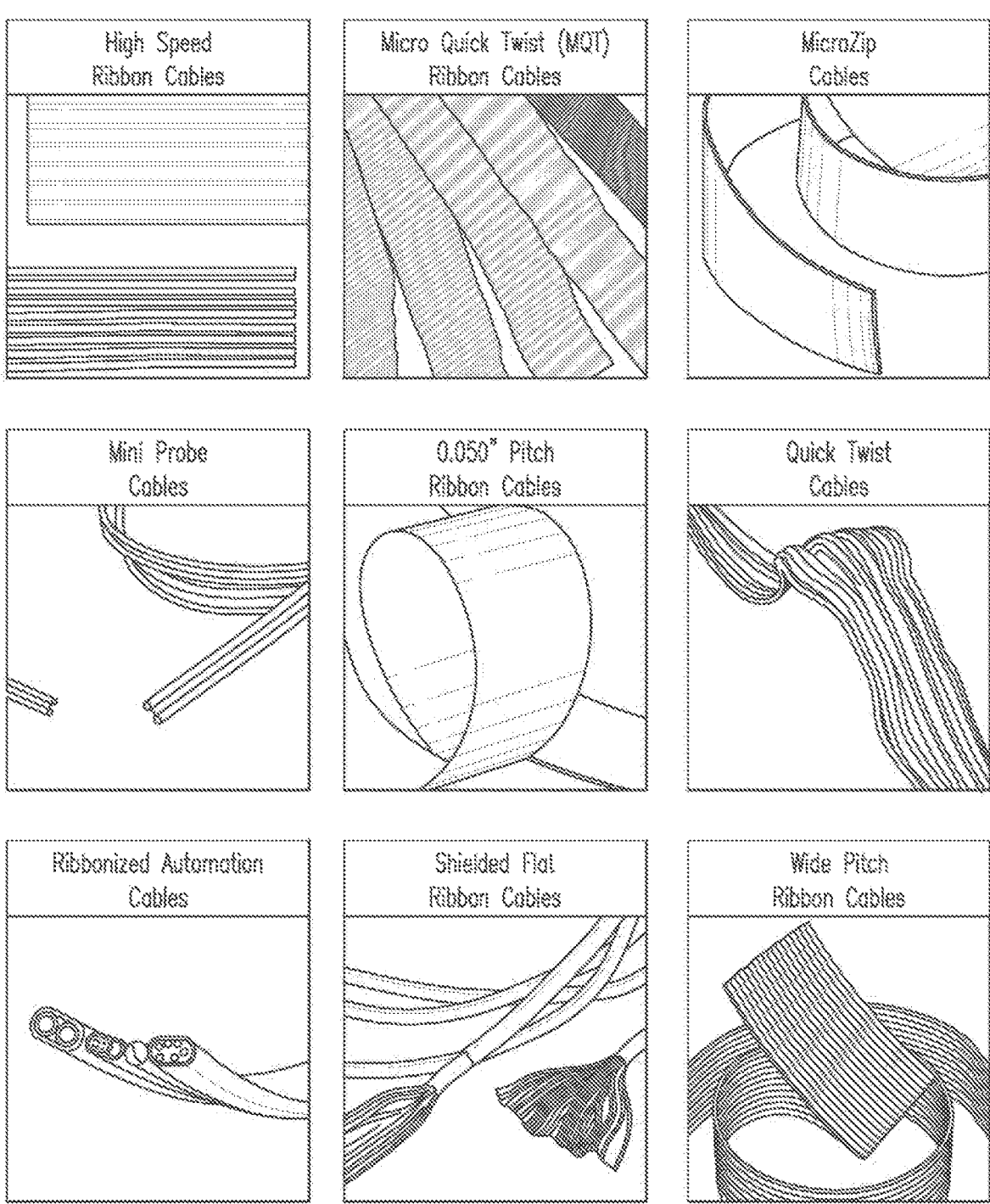

In another aspect, as shown in FIG. 4, an on-body analyte monitoring device 100 is provided. The on-body analyte monitoring device includes on body electronics 110 coupled to analyte sensor 402. In one embodiment, the analyte sensor 402 and on body electronics 110 are housed in a mounting unit 404. The mounting unit includes adhesive applied to the bottom surface to attach the on-body unit to a user.

As illustrated in FIG. 4, elongate interconnect conductive contact 206 can be in direct contact with analyte sensor 402 to establish electrical communication between the on body electronics 110 and sensor 402. When analyte sensor 402 is in contact with on body electronics 110, elongate member 204 can be compressed or collapsed and seal 210 forms a protective barrier around the connection from harmful elements (e.g., dust, liquid, dirt) between the on body electronics and sensor. In one embodiment, seal 210 is formed from a flexible polymer.

Seal 210 may be an individual molded component made of a flexible polymer, low durometer silicone, rubber or some other material TPE. In some embodiments, the interconnect extends approximately 1 mm beyond the face of seal 210. When on body electronics 110 is locked into position, elongate interconnect 204 compresses and makes contact with the conductive pads on analyte sensor 402. The seal also compresses to form a barrier around the perimeter of the interconnect/sensor connection. Interconnect 204 may function without the seal, however once liquid or dust got in, the interconnect/sensor interface may be compromised and fail.

In some embodiments, the seal 210 includes an opening to permit direct contact of a conductive contact disposed on the interconnect to the analyte sensor. In this manner, the analyte sensor and the on body electronics can establish electrical conductivity via the closed circuit provided by the interconnect.

In another embodiment, the elongate member 204 returns to its original configuration after analyte sensor 402 is disengaged from on body electronics 110. The signals generated by the analyte sensor relating to the measured analyte levels from biological fluid can be processed by the on body electronics 110 by the electrical contact between sensor 402 and on body electronics via contact plate 206 of interconnect.

The analyte sensor 402 employed in the on-body device, in some embodiments, comprises a substrate, one or more electrodes, a sensing layer and a barrier layer, as described below and disclosed in U.S. Pat. Nos. 6,284,478 and 6,990,366, the disclosures of which are incorporated herein by reference. As the sensor is employed by insertion and/or implantation into a user's body for a period of days, in some embodiments, the substrate is formed from a relatively flexible material to improve comfort for the user and reduce damage to the surrounding tissue of the insertion site, e.g., by reducing relative movement of the sensor with respect to the surrounding tissue.

Suitable materials for a flexible substrate include, for example, non-conducting plastic or polymeric materials and other non-conducting, flexible, deformable materials. Suitable plastic or polymeric materials include thermoplastics such as polycarbonates, polyesters (e.g., Mylar® and polyethylene terephthalate (PET)), polyvinyl chloride (PVC), polyurethanes, polyethers, polyamides, polyimides, or copolymers of these thermoplastics, such as PETG (glycol-modified polyethylene terephthalate). In other embodiments, the sensor includes a relatively rigid substrate. Suitable examples of rigid materials that may be used to form the substrate include poorly conducting ceramics, such as aluminum oxide and silicon dioxide. Further, the substrate can be formed from an insulating material. Suitable insulating materials include polyurethane, teflon (fluorinated polymers), polyethyleneterephthalate (PET, Dacron) or polyimide.

The sensor can include a distal end and a proximal end having different widths. In such embodiments, the distal end of the substrate may have a relatively narrow width. Moreover, sensors intended to be transcutaneously positioned into the tissue of a user's body can be configured to have a narrow distal end or distal point to facilitate the insertion of the sensor. For example, for insertable sensors designed for continuous or periodic monitoring of the analyte during normal activities of the patient, a distal end of the sensor which is to be implanted into the user has a width of 2 mm or less, preferably 1 mm or less, and more preferably 0.5 mm or less.

A plurality of electrodes is disposed near the distal end of the sensor. The electrodes can include a working electrode, counter electrode and reference electrode. Other embodiments, however, can include less or more electrodes. For example, as noted, a two electrode sensor can be utilized. Each of the electrodes is formed from conductive material, for example, a non-corroding metal or carbon wire. Suitable conductive materials include, for example, vitreous carbon, graphite, silver, silver-chloride, platinum, palladium, or gold. The conductive material can be applied to the substrate by various techniques including laser ablation, printing, etching, and photolithography. In one embodiment, each of the electrodes is formed from gold by a laser ablation technique. As further illustrated, the sensor can include conductive traces and extending from the one or more electrodes to respective contacts. In one embodiment, an insulating substrate (e.g., dielectric material) and electrodes can be arranged in a stacked orientation (i.e., insulating substrate disposed between electrodes. Alternatively, the electrodes can be arranged in a side by side orientation, as described in U.S. Pat. No. 6,175,752, the disclosure of which is incorporated herein by reference.

The sensor can include a sensing layer to facilitate the electrolysis of the analyte of interest. For example, the sensing layer can be an immobilized sensing layer comprising a catalyst and an electron transfer agent. Examples of immobilized sensing layers are described in U.S. Pat. Nos. 5,262,035, 5,264,104, 5,264,105, 5,320,725, 5,593,852, and 5,665,222, each of which is incorporated herein by reference. In some embodiments, the sensor can further include a barrier layer to act as a diffusion-limiting barrier to reduce the rate of mass transport of the analyte into the region around the working electrode. Examples of suitable barrier layers are described in U.S. Pat. Nos. 6,990,366 and 6,175,752, each of which is incorporated herein by reference.

In some embodiments, the sensor is a self-powered analyte sensor, which is capable of spontaneously passing a currently directly proportional to analyte concentration in the absence of an external power source. Any exemplary sensor is described in U.S. patent application Ser. No. 12/393,921, filed Feb. 26, 2009, entitled "Self-Powered Analyte Sensor," which is hereby incorporated by reference in its entirety herein for all purposes.

Figure 6:
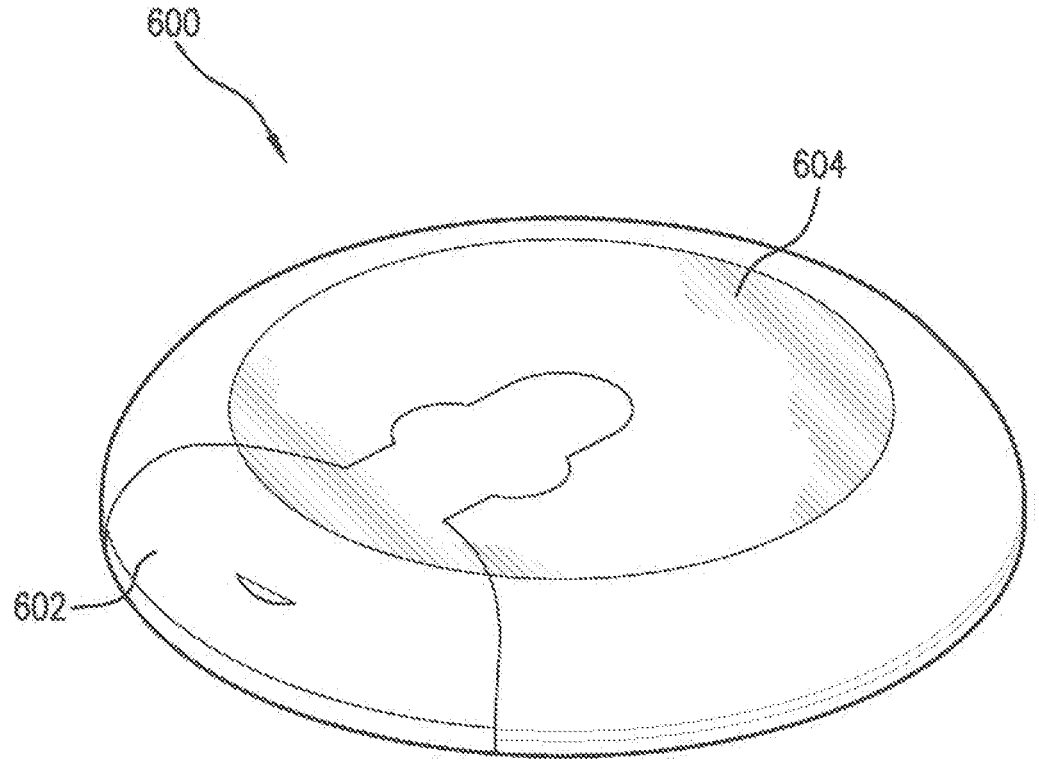
FIG. 6 depicts a pictorial view of an analyte monitoring device according to another embodiment of the present invention.
Figure 7A:
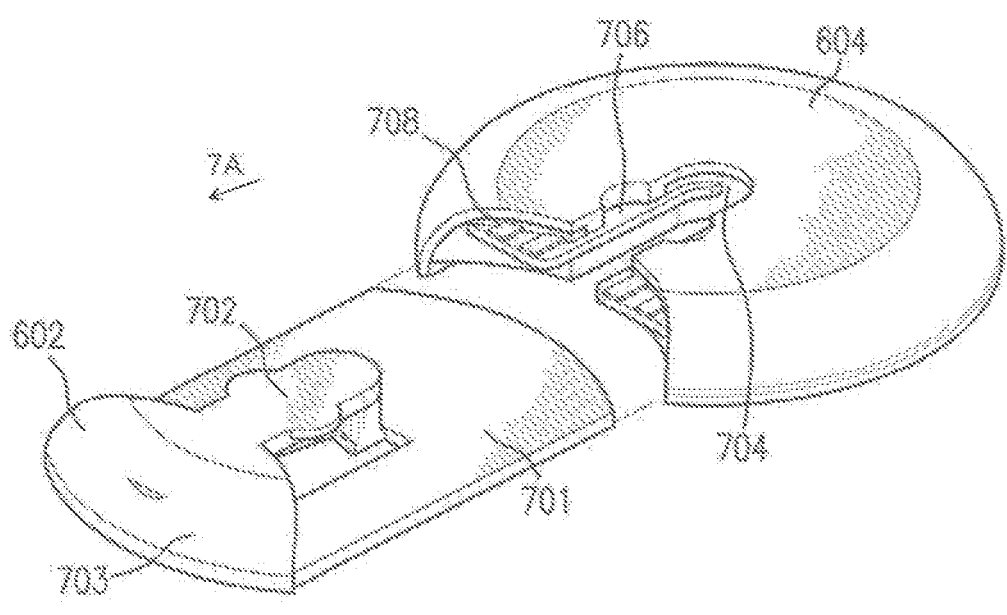
FIG. 7A depicts a pictorial view of the analyte monitoring device of FIG. 6 when it is disassembled.
Figure 7B:
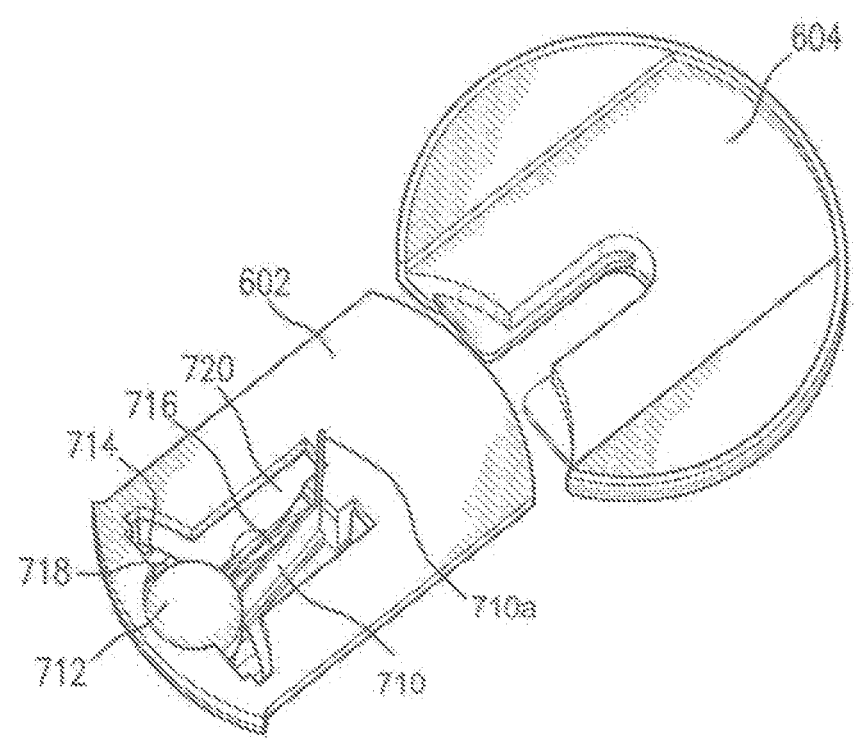
FIG. 7B depicts a bottom view of the on-body analyte monitoring device of FIG. 7A.
Figure 8:
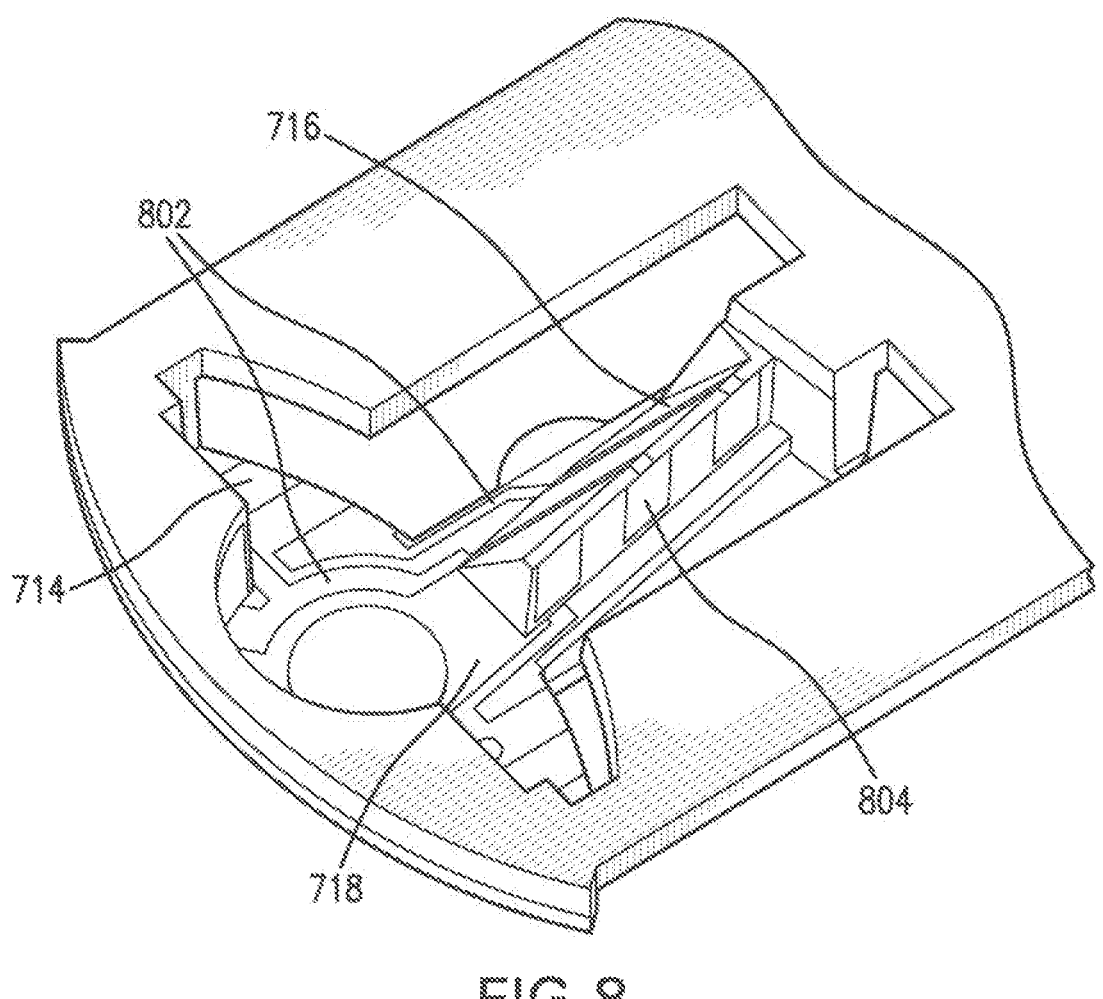
FIG. 8 depicts the interconnect of FIG. 7B with the battery and analyte sensor removed.

FIGS. 6, 7A-7B, and 8 illustrate on body electronics including a module interconnect in certain embodiments, with FIGS. 8 and 7A illustrate top perspective views, while FIGS. 7B and 8 illustrating bottom perspective views. Referring to FIGS. 6 and 7A, on body electronics 600 includes modular sensor assembly 604 which includes analyte sensor 710 (see e.g., FIG. 7B), for engageably coupling with electronics component 604. As illustrated, the modular sensor assembly 602 may be configured to interlock or otherwise engage with the electronics component 604. Accordingly, upon engagement of modular sensor assembly 602 and electronics component 604, on body electronics 600 with analyte sensor 710 may be provided.

In certain embodiments, modular sensor assembly 602 may be a molded device, such as for example, formed by injection molding techniques. As illustrated in FIG. 7A, modular sensor assembly 602 includes bottom surface 701 connected to top surface 702 by sidewall 703. As can be seen in the perspective views of FIGS. 7B and 8, in certain embodiments, top surface 702 includes conductive material 714 disposed thereon. Further, top surface 702 may include a vertical surface extending downwardly, which may include conductive material 716 disposed thereon. In certain embodiments, conductive material 716 includes conductive traces and/or conductive contacts.

Still referring to the figures, on body electronics 600 in certain embodiments include modular sensor assembly 602 and electronics component 604 configured for a slidable engagement. As illustrated in FIG. 7A, the bottom of electronics component 604 may include a surface configured to slidably receive modular sensor assembly 602. Further, in certain embodiments, top surface 702 of modular sensor assembly 602 may be configured to define a tongue to interlock with a corresponding groove 704 defined in electronics component 604 to define the shape of on body electronics 600.

Electronics component 604 in certain embodiments may include one or more PCBs including conductive material 708 disposed thereon, such as one or more conductive traces and/or conductive contacts. During engagement of electronics component 604 with modular sensor assembly 602, the conductive material 708 can interface with interconnect conductive material 714. Thus, during engagement, the electronics component 604 and modular sensor assembly 602 establishes electrical communication.

As illustrated in FIG. 7B, modular sensor assembly 602 includes analyte sensor 710 secured or otherwise coupled to a surface of the modular sensor assembly 602. For example, analyte sensor 710 may be coupled to the vertical surface extending from the top surface of the modular sensor assembly 602. In this manner, the vertical surface includes conductive material, such as conductive contacts 804 that connect with the one or more conductive contacts of analyte sensor 710 to establish an electrical communication between analyte sensor 710 and modular sensor assembly 602.

In certain embodiments, as best illustrated in FIGS. 7B and 8, analyte sensor 710 may be mounted to the sidewall of modular sensor assembly 602. In this embodiment, distal portion 710a of analyte sensor 710 is inserted perpendicular to the skin (not shown). In this regard, the bottom surface of the modular sensor assembly 602 includes an aperture 720 (FIG. 7B) to permit the distal portion 710a of analyte sensor 710 to extend from the bottom of on body electronics 600 such that distal portion 710a of analyte sensor 710 may be implanted into the body of a user when in use. In certain embodiments, modular sensor assembly 602 may also include a power source 712, such as a battery. Power source 712 may provide power via conductive traces 714 to the electronics component 604. In this manner, the electronics component 604 may be powered by power source 712 of modular sensor assembly 602 such that the electronics component 604 does not need an internal power source.

The conductive material disposed on the modular sensor assembly 602 and/or the electronics component 604 and analyte sensor 710 may include conductive film, such as, but not limited to, an anisotropic film. Conductive material, such as the conductive film and/or the Zebra style connector, can provide both a mechanical and electrical connection between modular sensor assembly 602 and sensor 710 or electronics component 604. Modular sensor assembly 602, analyte sensor 710, and electronics component 604 may also be bonded together utilizing an adhesive, such as a UV curable adhesive, or a multi-adhesive, such as a silver loaded epoxy can be used. Other adhesives can alternatively be employed.

The sensor and the on body electronics can establish electrical communication by way of the interconnect. In this manner, the one or more electrodes of the analyte sensor generate a signal relative to the analyte levels depicted in the bodily fluid of the user, the conductive traces permit the signal to travel to the conductive contacts of the sensor which is in electrical communication with the conductive material, e.g., conductive contacts 804 of the interconnect. By way of the conductive traces 716 and 802, which establish electrical communication with the on body electronics 600, the signals relative to the analyte levels are communicated to the on body electronics 600. The bottom surface of the on body electronics 600 and/or modular sensor assembly 602 can include an adhesive to attach to the skin of the user. Thus, the interconnect can serve as a mounting unit for the on-body monitoring device to be worn by a user. The on-body analyte monitoring device, as described above, can be employed as a component of an analyte monitoring system, such as the systems illustrated in FIGS. 1A and 1B.

On body electronics 600 may be mounted to the user as one component or separately. For example, with reference to FIG. 7A, the modular sensor assembly 602 may be first mounted on the skin such that the distal portion 710a (not shown) of the sensor 710 is at least partially inserted into the skin. An adhesive (not shown) is used to fix modular sensor assembly 602 to the skin. Subsequently, the electronics component 604 may be attached to modular sensor assembly 602, for example, by sliding the electronics component 604 in the direction of arrow 7A, such that the modular sensor assembly 602 and electronics component 604 are secured together. In some embodiments, the electronics component 604 is mounted first and the modular sensor assembly 602 is mounted subsequently.

In some embodiments, the modular sensor assembly 602 and electronics component 604 are secured together, and then subsequently mounted onto the patient as a single unit 600. Insertion of electronics unit 600 by an inserter, such as inserter 150 (FIG. 1B) is further described as an insertion device, e.g., as described in U.S. patent application Ser. No. 12/698,129 filed on Feb. 1, 2010 and U.S. Provisional Application Nos. 61/238,646, 61/246,825, 61/247,516, 61/249,535, 61/317,243, 61/345,562, and 61/361,374, the disclosures of each of which are incorporated herein by reference for all purposes.

In some embodiments, the analyte monitoring system 100 can include a secondary receiver unit 106 which is operatively coupled to the communication link and configured to receive data transmitted from the on body electronics 110. Moreover, the secondary receiver unit 106 can be configured to communicate with the display unit 120 as well as a data processing terminal 170. The secondary receiver unit 106 may be configured for bi-directional wireless communication with each or one of the display unit 104 and the data processing terminal 170.

In one embodiment, the secondary receiver unit 106 may be configured to include a limited number of functions and features as compared with the display unit 104. As such, the secondary receiver unit 106 may be configured substantially in a smaller compact housing or embodied in a device such as a wrist watch, pager, mobile phone, PDA, for example. Alternatively, the secondary receiver 106 may be configured with the same or substantially similar functionality as the display unit 104. The receiver unit may be configured to be used in conjunction with a docking cradle unit, for example for one or more of the following or other functions: placement by bedside, for re-charging, for data management, for night time monitoring, and/or bi-directional communication device.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby. Additional detailed description of embodiments of the disclosed subject matter are provided in, but not limited to: U.S. Pat. Nos. 7,299,082; 7,167,818; 7,041,468; 6,942,518; 6,893,545; 6,881,551; 6,773,671; 6,764,581; 6,749,740; 6,746,582; 6,736,957; 6,730,200; 6,676,816; 6,618,934; 6,616,819; 6,600,997; 6,592,745; 6,591,125; 6,560,471; 6,540,891; 6,514,718; 6,514,460; 6,503,381; 6,461,496; 6,377,894; 6,338,790; 6,299,757; 6,284,478; 6,270,455; 6,175,752; 6,161,095; 6,144,837; 6,143,164; 6,121,009; 6,120,676; 6,071,391; 5,918,603; 5,899,855; 5,822,715; 5,820,551; 5,628,890; 5,601,435; 5,593,852; 5,509,410; 5,320,715; 5,264,014; 5,262,305; 5,262,035; 4,711,245; 4,545,382; 5,356,786; 5,543,326; 6,103,033; 6,134,461; 6,143,164; 6,144,837; 6,161,095; 6,579,690; 6,605,200; 6,605,201; 6,618,934; 6,654,625; 6,676,816; 6,730,200; 6,736,957; 6,932,892; U.S. Publication No. 2004/0186365, now U.S. Pat. No. 7,811,231; U.S. Publication No. 2005/0182306, now U.S. Pat. No. 8,771,183; U.S. Publication No. 2006/0025662, now U.S. Pat. No. 7,740,581; U.S. Publication No. 2006/0091006; U.S. Publication No. 2007/0056858, now U.S. Pat. No. 8,298,389; U.S. Publication No. 2007/0068807, now U.S. Pat. No. 7,846,311; U.S. Publication No.

2007/0095661; U.S. Publication No. 2007/0108048, now U.S. Pat. No. 7,918,975; U.S. Publication No. 2007/0199818, now U.S. Pat. No. 7,811,430; U.S. Publication No. 2007/0227911, now U.S. Pat. No. 7,887,682; U.S. Publication No. 2007/0233013; U.S. Publication No. 2008/0066305, now U.S. Pat. No. 7,895,740; U.S. Publication No. 2008/0081977, now U.S. Pat. No. 7,618,369; U.S. Publication No. 2008/0102441, now U.S. Pat. No. 7,822,557; U.S. Publication No. 2008/0148873, now U.S. Pat. No. 7,802,467; U.S. Publication No. 2008/0161666; U.S. Publication No. 2008/0267823; U.S. Publication No. 2009/0054748, now U.S. Pat. No. 7,885,698; U.S. patent application Ser. No. 10/745,878, filed Dec. 26, 2003, now U.S. Pat. No. 7,811,231, and entitled "Continuous Glucose Monitoring System and Methods of Use", U.S. patent application Ser. No. 12/143,731, filed Jun. 20, 2008, now U.S. Pat. No. 8,597,188, and entitled "Health Management Devices And Methods"; U.S. patent application Ser. No. 12/143,734, filed Jun. 20, 2008, now U.S. Pat. No. 8,617,069, and entitled "Health Monitor"; U.S. Provisional Patent Application No. 61/149,639, filed Feb. 3, 2009, and entitled "Compact On-Body Physiological Monitoring Devices And Methods Thereof"; U.S. Provisional Application No. 61/291,326, filed Dec. 30, 2009, and U.S. Provisional Application No. 61/299,924 filed Jan. 29, 2010; U.S. patent application Ser. No. 11/461,725, now U.S. Pat. No. 7,866,026; U.S. patent application Ser. No. 12/131,012; U.S. patent application Ser. No. 12/242,823, now U.S. Pat. No. 8,219,173; U.S. patent application Ser. No. 12/363,712, now U.S. Pat. No. 8,346,335; U.S. patent application Ser. No. 12/698,124; U.S. patent application Ser. No. 12/698,129; U.S. patent application Ser. No. 12/714,439; U.S. patent application Ser. No. 12/794,721, now U.S. Pat. No. 8,595,607; U.S. patent application Ser. No. 12/842,013; U.S. Patent Application No. 61/238,646; U.S. Patent Application No. 61/345,562; U.S. Patent Application No. 61/361,374; and elsewhere, the disclosures of each are incorporated by reference in their entirety herein for all purposes.

What is claimed is:

1. An on-body analyte monitoring device, comprising:
an analyte sensor configured to measure analyte levels in a user's body, the analyte sensor comprising:
a proximal portion;
a distal portion configured to be in fluid contact with a bodily fluid of the user; and
a plurality of electrodes configured to generate one or more signals indicative of the analyte levels in the bodily fluid;
an electronics unit configured to receive the one or more signals, the electronics unit comprising a housing having a top surface, a bottom surface, and defining an inner space therebetween, the electronics unit further comprising a printed circuit board (PCB) disposed within the inner space; and
a flexible interconnect body comprising a conductive material, the flexible interconnect body further comprising a first portion, a second portion, and an at least partially curved portion between the first portion and the second portion, and
wherein the first portion is in electrical contact with the PCB,
wherein the at least partially curved portion is in electrical contact with the proximal portion of the analyte sensor;
wherein the first portion and the second portion are disposed within the inner space, and wherein at least part of the at least partially curved portion is disposed outside the housing; and wherein the second portion is in contact with the housing.

2. The on-body analyte monitoring device of claim 1, wherein the second portion of the flexible interconnect body is in contact with non-conductive material.

3. The on-body analyte monitoring device of claim 1, wherein electrical communication is established between the analyte sensor and the electronics unit through the flexible interconnect body.

4. The on-body analyte monitoring device of claim 1, wherein the conductive material of the flexible interconnect body is elastomeric.

5. The on-body analyte monitoring device of claim 1, wherein the flexible interconnect body is configured to form a closed circuit with the electronics unit and the analyte sensor when the first portion is in electrical contact with the PCB and the at least partially curved portion is in electrical contact with the proximal portion of the analyte sensor.

6. The on-body analyte monitoring device of claim 1, wherein the plurality of electrodes includes at least a working electrode and a reference electrode.

7. The on-body analyte monitoring device of claim 1, wherein the plurality of electrodes are arranged in a side-by-side orientation.

8. The on-body analyte monitoring device of claim 1, wherein the proximal portion of the analyte sensor comprises a first width, and wherein the distal portion of the analyte sensor comprises a second width less than the first width.

9. The on-body analyte monitoring device of claim 1, wherein the analyte sensor further comprises a sensing layer configured to react with analytes in the bodily fluid of the user.

10. The on-body analyte monitoring device of claim 1, wherein the analyte sensor is further configured to be inserted into a skin surface of the user at an angle perpendicular to the skin surface.

11. The on-body analyte monitoring device of claim 1, wherein the analyte sensor is a glucose sensor.

12. The on-body analyte monitoring device of claim 1, further comprising a mounting unit having a bottom surface, wherein the bottom surface comprises an adhesive layer configured to attach to a skin surface of a user.

13. The on-body analyte monitoring device of claim 12, wherein the analyte sensor is further configured to couple with the mounting unit.

14. The on-body analyte monitoring device of claim 1, further comprising a battery disposed within the inner space of the electronics unit.

15. The on-body analyte monitoring device of claim 1, wherein the conductive material on the flexible interconnect body comprises a first conductive area and a second conductive area, wherein the first conductive area contacts the PCB and establishes an electrical communication between the PCB and the flexible interconnect body, and wherein the second conductive area contacts the analyte sensor and establishes electrical communication between the flexible interconnect body and the analyte sensor.

16. The on-body analyte monitoring device of claim 1, further comprising a seal comprising a flexible polymer, wherein the seal is configured to form a protective barrier around the electronics unit and the analyte sensor.

17. The on-body analyte monitoring device of claim 16, wherein the flexible polymer comprises a rubber material.

18. The on-body analyte monitoring device of claim 1, wherein the first portion is in electrical contact with the PCB along a first axis, wherein the at least partially curved portion is in electrical contact with the proximal portion of the analyte sensor along a second axis that is not parallel to the first axis.

19. The on-body analyte monitoring device of claim 1, wherein the flexible interconnect body is in a partially compressed state when the at least partially curved portion is in electrical contact with the proximal portion of the analyte sensor.

* * * * *